United States Patent
Schultz et al.

(10) Patent No.: US 11,087,453 B2
(45) Date of Patent: Aug. 10, 2021

(54) AUTOMATED FAILURE DETECTION FOR MEDICAL DEVICE TESTING SYSTEMS AND METHODS

(71) Applicant: DYNATEK LABS, INC., Galena, MO (US)

(72) Inventors: Mark Alan Schultz, Billings, MO (US); Donald John Rohde, Springfield, MO (US); Christopher Conti, Galena, MO (US)

(73) Assignee: DYNATEK LABS, INC., Galena, MO (US)

( * ) Notice: Subject to any disclaimer, the term of this patent is extended or adjusted under 35 U.S.C. 154(b) by 0 days.

(21) Appl. No.: 16/437,809

(22) Filed: Jun. 11, 2019

(65) Prior Publication Data

US 2019/0378261 A1 Dec. 12, 2019

Related U.S. Application Data

(60) Provisional application No. 62/683,396, filed on Jun. 11, 2018.

(51) Int. Cl.
| | |
|---|---|
| *H04N 7/18* | (2006.01) |
| *G06T 7/00* | (2017.01) |
| *G06T 7/13* | (2017.01) |
| *G06T 7/174* | (2017.01) |
| *A61F 2/90* | (2013.01) |

(52) U.S. Cl.
CPC ............... *G06T 7/001* (2013.01); *A61F 2/90* (2013.01); *G06T 7/13* (2017.01); *G06T 7/174* (2017.01); *A61F 2240/008* (2013.01); *G06T 2207/10016* (2013.01); *G06T 2207/30052* (2013.01); *G06T 2207/30136* (2013.01)

(58) Field of Classification Search
CPC ...................................................... G06T 7/001
USPC ........................................................... 348/92
See application file for complete search history.

(56) References Cited

U.S. PATENT DOCUMENTS

| | | | | |
|---|---|---|---|---|
| 5,670,708 A | * | 9/1997 | Vilendrer | G01M 99/00 73/37 |
| 5,779,729 A | * | 7/1998 | Severini | A61L 31/10 128/898 |
| 6,535,618 B1 | | 3/2003 | Rhoads | |
| 6,810,751 B2 | | 11/2004 | Moreno et al. | |

(Continued)

OTHER PUBLICATIONS

"Gong et al. Fatigue to Fracture: An Informative, Fast, and Reliable Approach for Accessing Medical Implant Durability, 3 Journal of ASTM International, vol. 6, No. 7, Paper ID JAI102412, 10 pages."

(Continued)

*Primary Examiner* — Leron Beck
(74) *Attorney, Agent, or Firm* — Kutak Rock LLP; James H. Jeffries

(57) ABSTRACT

Systems and methods are described for capturing images of articles under test and processing the images to automatically detect the failure of a test article. The described methods include optimizing image capture to allow for the use of low cost imaging devices instead of high speed cameras or other expensive equipment. The described methods also include several methods for processing the images to identify the occurrence of a failure event.

45 Claims, 11 Drawing Sheets

(56) References Cited

U.S. PATENT DOCUMENTS

| | | | | |
|---|---|---|---|---|
| 6,881,224 | B2* | 4/2005 | Kruse | A61F 2/2472 |
| | | | | 623/2.11 |
| 7,254,988 | B2 | 8/2007 | Keeble | |
| 7,363,821 | B2* | 4/2008 | Black | G01N 3/32 |
| | | | | 73/810 |
| 7,621,192 | B2 | 11/2009 | Conti et al. | |
| 8,017,396 | B2* | 9/2011 | Kumar | A61F 2/2415 |
| | | | | 435/402 |
| 8,081,307 | B2* | 12/2011 | Cameron | A61F 2/915 |
| | | | | 356/237.1 |
| 8,196,478 | B2 | 6/2012 | Lorenz et al. | |
| 8,237,789 | B2* | 8/2012 | Maehringer-Kunz | |
| | | | | G01N 21/952 |
| | | | | 348/92 |
| 8,311,312 | B1* | 11/2012 | Richardson | G01N 21/95 |
| | | | | 382/141 |
| 8,490,504 | B2 | 7/2013 | Weinberg et al. | |
| 8,811,691 | B2* | 8/2014 | Freifeld | G01N 21/952 |
| | | | | 382/128 |
| 9,071,829 | B2* | 6/2015 | Michot | G06T 7/77 |
| 9,417,110 | B2 | 8/2016 | Raz et al. | |
| 10,605,700 | B2 | 3/2020 | Conti et al. | |
| 2003/0110830 | A1 | 6/2003 | Dehdashtian et al. | |
| 2003/0125804 | A1 | 7/2003 | Kruse et al. | |
| 2006/0058617 | A1* | 3/2006 | Sano | A61B 1/0005 |
| | | | | 600/407 |
| 2006/0155184 | A1* | 7/2006 | Florent | G06T 7/149 |
| | | | | 600/407 |
| 2006/0275340 | A1* | 12/2006 | Udipi | A61L 31/06 |
| | | | | 424/426 |
| 2007/0293932 | A1* | 12/2007 | Zilla | A61B 5/1076 |
| | | | | 623/1.11 |
| 2008/0245952 | A1* | 10/2008 | Troxell | H04N 5/2354 |
| | | | | 250/208.1 |
| 2008/0294038 | A1* | 11/2008 | Weese | A61B 6/507 |
| | | | | 600/431 |
| 2009/0035449 | A1* | 2/2009 | Chen | B05B 13/0228 |
| | | | | 427/2.25 |
| 2010/0225478 | A1 | 9/2010 | McCloskey et al. | |
| 2010/0313683 | A1* | 12/2010 | Nickel | G01N 3/12 |
| | | | | 73/863 |
| 2014/0341528 | A1 | 11/2014 | Mahate et al. | |
| 2015/0016661 | A1 | 1/2015 | Lord | |
| 2017/0030842 | A1* | 2/2017 | Laguarta Bertram | |
| | | | | G01B 11/2408 |
| 2017/0227426 | A1 | 8/2017 | Conti et al. | |
| 2017/0295300 | A1* | 10/2017 | Esashi | A61B 6/504 |
| 2019/0339168 | A1 | 11/2019 | Conti et al. | |
| 2020/0126229 | A1* | 4/2020 | Lavi | A61B 6/02 |

OTHER PUBLICATIONS

"Kemp et al. Instron Medical Device and Biomaterials Markets, Testing of Stents and Stent Materials, pp. 1-4".

"Non Final Office Action Received for U.S. Appl. No. 15/424,689, dated Jan. 24, 2019, 17 pages".

"Pitney et al.. Longitudinal Stent Deformation: Important of Stent Type and Stent Apposition, American Journal of 2 Biomedical Engineering 2013, 3(3): pp. 63-69."

"Notice of Allowance Received for U.S. Appl. No. 16/419,549 , dated Dec. 18, 2019."

"Notice of Allowance Received for U.S. Appl. No. 15/424,689, dated Nov. 25, 2019, 16 pages".

* cited by examiner

AUTOMATED FAILURE DETECTION FOR MEDICAL DEVICE TESTING SYSTEMS AND METHODS

CROSS-REFERENCE TO RELATED APPLICATIONS

This application claims the benefit of U.S. Provisional Patent Application Ser. No. 62/683,396 filed on Jun. 11, 2018, the disclosure of which is incorporated herein by reference.

BACKGROUND

Field of the Invention

The invention generally relates to systems and methods for determining the occurrence of a failure of a medical device during testing of a test article of the medical device. In some embodiments, the testing methodology is fatigue testing or fatigue-to-fracture testing of a medical device. In some embodiments, the system automatically identifies the failure event. More specifically, the invention relates to systems and methods for determining the occurrence of a failure event during fatigue or stress testing, or fatigue-to-fracture testing, of one or more test articles of a medical device. The failure event may be identified by changes in the structure of the test article or other indicators of the occurrence of the failure event. In many embodiments, the invention relates to the testing of implantable medical devices such as implantable medical stents, grafts, valves, and other such devices.

Modern medical procedures routinely include deploying implants into a patient's vascular system to perform various therapeutic functions. Prosthetic vascular implants, such as heart valves, stents, grafts, mesh tubes, and stent-grafts used for human implantation are subjected to the continuous fluctuating stress of pulsatile blood pressure. As an example, tubular mesh samples or stents are often inserted in an artery of a patient to maintain a flow lumen through the artery at a location that had previously been at least partially blocked or occluded. It is therefore necessary to test such implants to prove their durability over a lifetime of exposure to pulsatile blood pressure.

Ideally such stents, mesh tubes, or other vascular prostheses, are able to withstand the dynamic physiological conditions that occur within the vessel or organ in which they are emplaced. For instance, in the abdominal aorta, blood pressure in the average healthy subject is 120 mmHg/80 mmHg, i.e. the blood pressure varies by 40 mmHg for every pulse. Compliance of a healthy aorta can be of the order of 20-25% per 100 mmHg so that a change in vasculature diameter of 8 to 10% can be expected at every heartbeat. In order to simulate such a change in diameter, some testing methodologies employ a pulse pressure between 80 mmHg and 120 mmHg. In order to test medical devices to be implanted in such conditions, systems and devices have been developed for testing medical devices under simulated physiological dynamic loading conditions.

Some testing methodologies rely on fatigue testing, or testing to success, by testing a medical device for a certain number of cycles and deeming the test successful if the medical device does not fail during the testing. In some methods of testing to success, vascular medical devices are tested for 400,000,000 cycles which represent approximately 10 years of implantation life at a heart rate of 80 beats per minute. These tests may be performed under simulated physiological dynamic loading conditions and with accelerated pulse rates to shorten the duration of the test.

Testing to success is indicative of the durability of the stent under physiological conditions of systolic/diastolic pressures encountered in accelerated radial pulsatile durability testing. However, testing to success does not predict the endurance limit or fatigue life of the device. After a successful "testing to success" or fatigue test there is no way to know under what conditions, including conditions that may exceed physiological parameters, the stent, stent-graft, or other medical device would fail.

An alternative testing method is a "fatigue-to-fracture" approach. This methodology involves a combination of Finite Element Analysis (FEA) modeling and in vitro testing to assess the durability of stents or other medical devices through established fracture mechanics techniques. This methodology of testing allows the determination of a stress loading level at which the tested device should never fail under normal physiological conditions.

Knowing when and where fracture, secondary fracture, or other failure, of the implantable medical device, stent, mesh tubes, grafts, valves, or other prosthesis, is most likely to occur under a variety of simulations is ideal for device development. Manufacturers can then use this information to design their product with the knowledge gained by multiple test methodologies, including fatigue testing and fatigue-to-fracture analysis. Determining the approximate fatigue and endurance location limits of the stent, or other prosthesis, helps accomplish the provision of a suitable stent, or other prosthesis for use in patients.

While described in relation to embodiments for testing medical devices such as stents, the systems and methods described herein could also be utilized to automate testing for other types of testing processes and devices. For example, the systems and methods described herein could be used to monitor the testing of heart valves, stitching of material around heart valves, grafts, stent-grafts, silicone tubes, elastic devices, and fabrics to test the degradation and fatigue of the materials.

Furthermore, the inventive systems and methods described herein allow for the use of low cost camera and processor systems instead of more expensive measuring systems such as high speed cameras or laser micrometer systems.

SUMMARY OF THE INVENTION

In various embodiments, the system comprises a mock vessel for testing an article such as an implantable medical device, a camera for capturing images of the test article, a signal processor configured to capture, receive, and process images from the camera to automatically detect failure of the test article, and a notification system for providing notification of failure events.

In various embodiments, the methods comprise methods of processing the images captured by the camera using the signal processor characterize the structure of the test article, identify changes in the structure of the test article over time, record data regarding the changes for later analysis, and provide notification of the event of failure events upon their occurrence.

In some embodiments, the signal processor utilizes indicator lights to select images taken at desired times for analysis. In other embodiments, an array of indicator lights is provided to allow the use of a camera with a rolling shutter to allow the signal processor to select only portions of an image that were captured at the desired time for further analysis.

In other embodiments, the signal processor utilizes statistical processes to characterize the structure of the test article and determine when a structural failure has occurred in the test article.

DETAILED DESCRIPTION

The systems and methods described herein are described in relation to embodiments used to detect fractures or other failure events produced during the testing of devices such as implantable medical devices. In some embodiments, the implantable medical devices under test are subject to conditions similar to those found in their intended implanted environment, which in the main case of interest is the human body. In some embodiments, the testing provides simulation of a heart beat with blood pressures at a differential pressure such as 80 mmHg for a low (diastolic) pressure and 120 mmHg for a higher (systolic) pressure. In some embodiments, other simulated blood pressure conditions may be selected for the test. In various embodiments, the heart rate is simulated at typical 72 beats per minute, though other embodiments may use varying heart rates for testing purposes. In a preferred embodiment, the temperature is kept approximately at a typical human body temperature of 37 degrees C. FDA approved stents usually undergo 400 million cycles of testing which represents about 10 years of use. Since testing a stent for 10 years is not realistic, accelerated testing is used where the pulse rate is increased while maintaining the same pressure and other conditions.

If the goal of the test is to understand how the stent mechanically fractures over time, the pressure and sometimes the temperature are increased along with the pulse rate. In such embodiments, hyper-physiological conditions may be utilized to cause the device to fail as in the "fatigue to fracture" testing methodology.

Figure 1A:
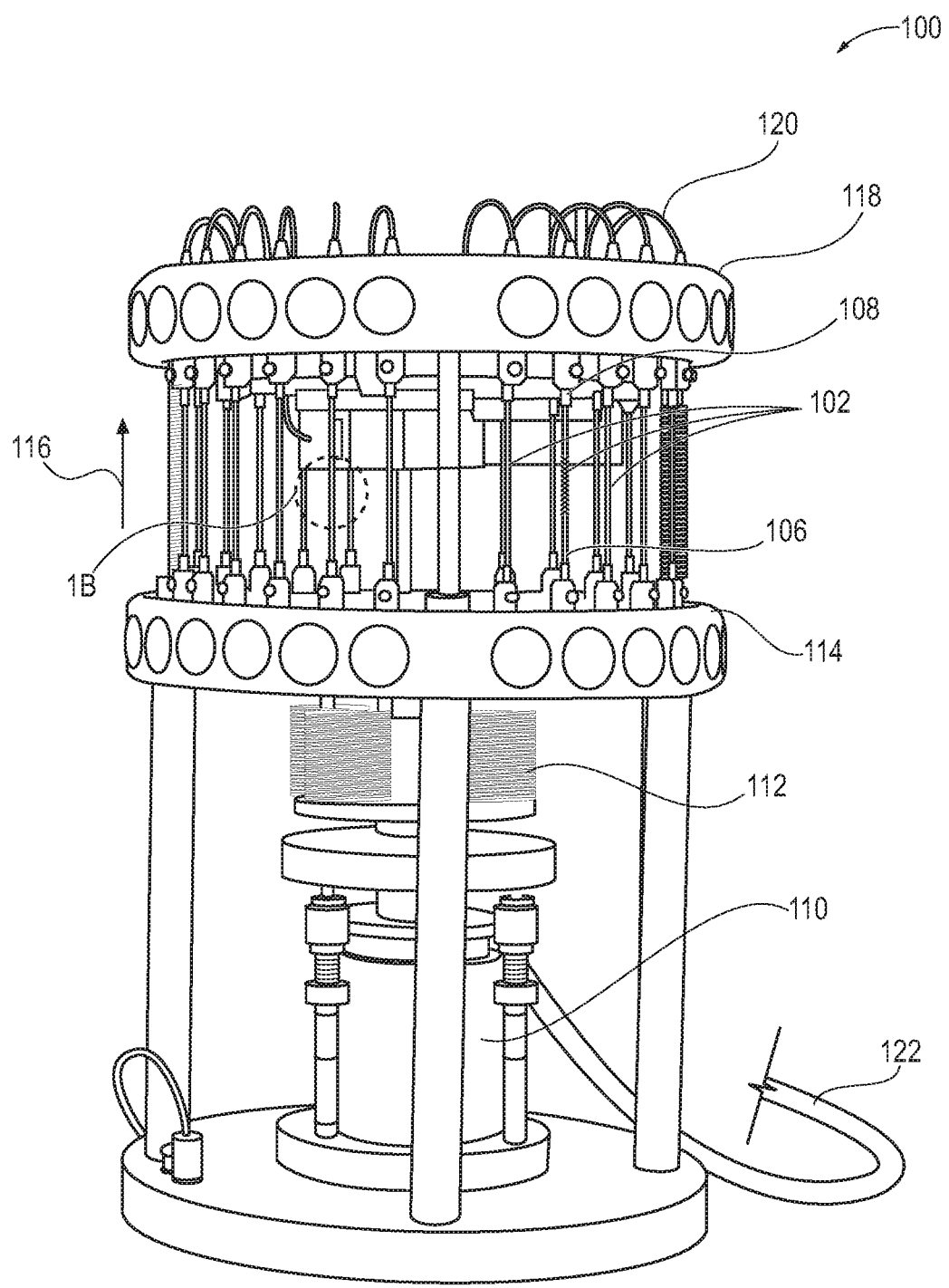
FIG. 1A is a perspective view of a testing system for simultaneously testing multiple implantable medical devices.

In one embodiment, the method utilizes a testing system, one or more cameras, a signal processor, and a notification device. Referring now to FIG. 1A, a testing system 100 is depicted for testing multiple test articles simultaneously. One or more cameras 134 (not shown in FIG. 1A) may be utilized with such a system to capture images of the test articles during testing. In some embodiments, the testing system 100 comprises one or more mock vessels 102 in which a test article 104 is deployed for testing. As can be seen most clearly in FIG. 1D, the depicted embodiment of the mock vessel 102 has an outer surface 126, an inner surface 128, and a lumen 132. The depicted test article is deployed in the lumen 132 against the inner surface 128 of the mock vessel 102. The inlet 106 and outlet 108 of the mock vessel 102 are then attached to the testing system 100 so that fluid may be pumped through the mock vessels 102 to subject the test article 104 to the desired testing conditions.

The depicted embodiment of the testing system 100 has a motor 110 to power the bellows 112 that drive the fluid through the mock vessels 102 in the direction indicated by arrow 116. Some embodiments have an inlet manifold 114 and an outlet manifold 116 to direct fluid flow through the mock vessels 102. Other tubing 120 and return line 122 may be used to create a circuit for the fluid to cycle through the system 100. The type of pump or particular connection of tubing and piping shown in FIG. 1A is exemplary and not limiting of the inventive systems and methods claimed herein.

Figure 1B:
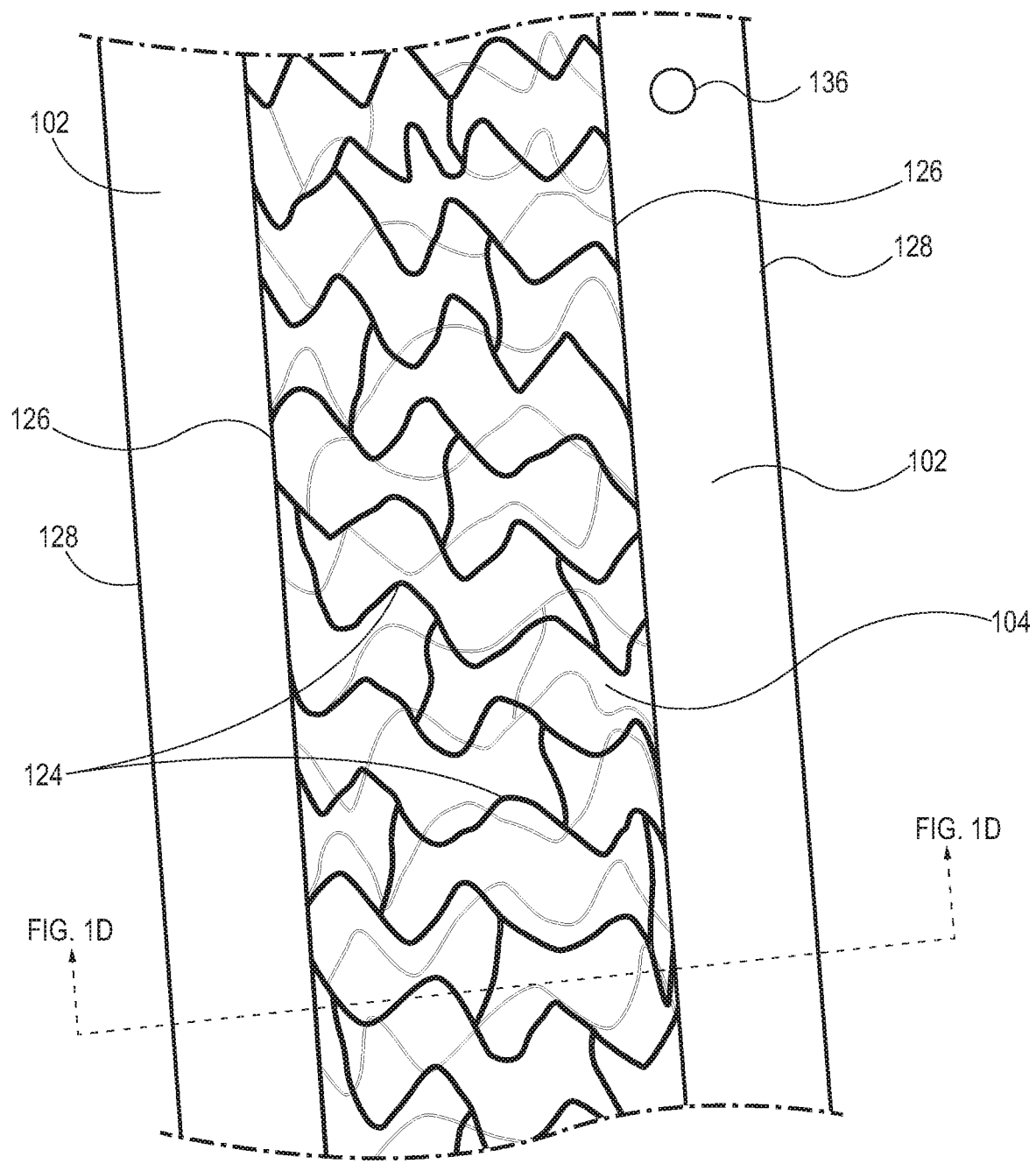
FIG. 1B is a detailed view of an implantable medical device installed in a testing system.
Figure 1C:
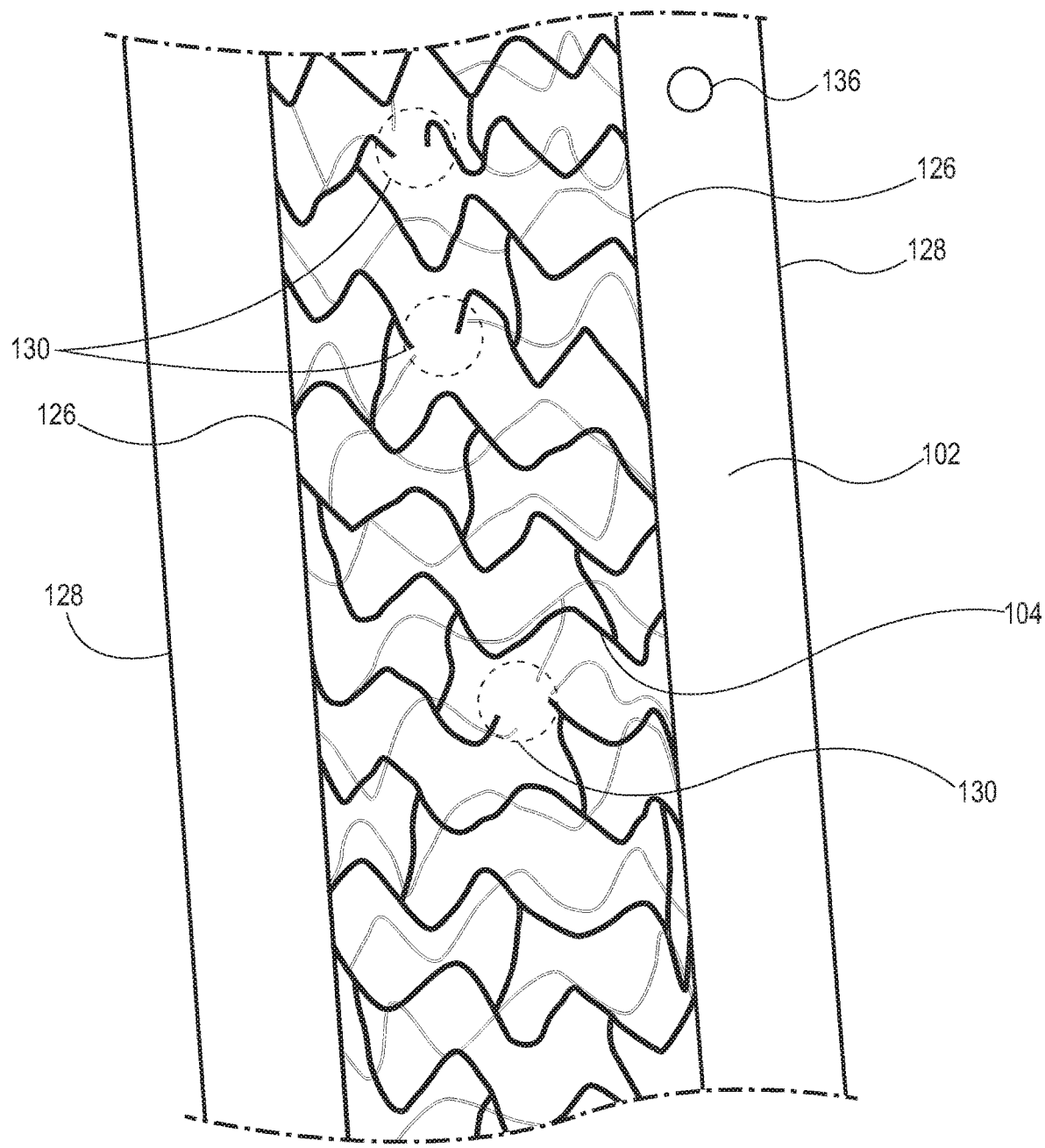
FIG. 1C is a detailed view of an implantable medical device installed in a testing system.

Referring now to FIGS. 1B and 1C, views of a portion of an embodiment of the inventive system 100 during testing of a test article are depicted. Specifically portions of the mock vessel 106 in which the test article 104 are deployed are depicted in these figures. The mock vessel 106 comprises a transparent tubular element that, in this case, simulates a blood vessel. Disposed within the mock vessel 106 is test article 104 of the medical device. In the depicted embodiment the test article 104 is a stent for use in a blood vessel. A fluid to simulate blood is pumped through the mock vessel 106 with an oscillating pressure that simulates the human pulse and blood flow.

The views in FIGS. 1B and 1C simulate the images captured by a camera 134 during use of the system. The views in both FIGS. 1B and 1C are of the same mock vessel 106 and test article 104 but taken at different times. In the depicted embodiment, an optional light 136 is visible in the field of view in both images that is controlled by the testing system 100 to indicate the occurrence of certain events, such as the timing of high and low pressure peaks. In images taken at a first time with a minimal pressure the light 136 is red. In images taken at a second time with a maximum pressure the light 136 is green. The test article 104 in FIGS. 1B and 1C comprises a stent formed from a tube of metal mesh made of wires 124. When the stent 104 is functioning properly images taken at the varying pressures are substantially identical with respect to the positions of the wires 124 that make up the mesh tube stent. When the wires 124 that form the mesh tube fail by breaking, the broken wires 130 are visible in images taken at the high pressure time such as shown by FIG. 1C. In some embodiments, the broken wires may also be visible at other times in the pressure cycle as well.

An example of such breakage of wires 124 may be seen by comparing areas 130 in FIGS. 1B and 1C. The discontinuity in the wire 124 can be clearly seen in FIG. 1C. When such breakage does occur, a variety of techniques may be used within various embodiments of the inventive system to detect the failure. In some embodiments, the system may analyze the images taken at minimum and maximum pressures to make measurements of specific characteristics of the test article and compare them for changes, such as stent width measurements, stent edge measurements relative to a line defining an imaginary edge of the stent, or measuring from abstract points in the picture such as an arbitrary pixel to the closest stent edge.

Figure 1D:
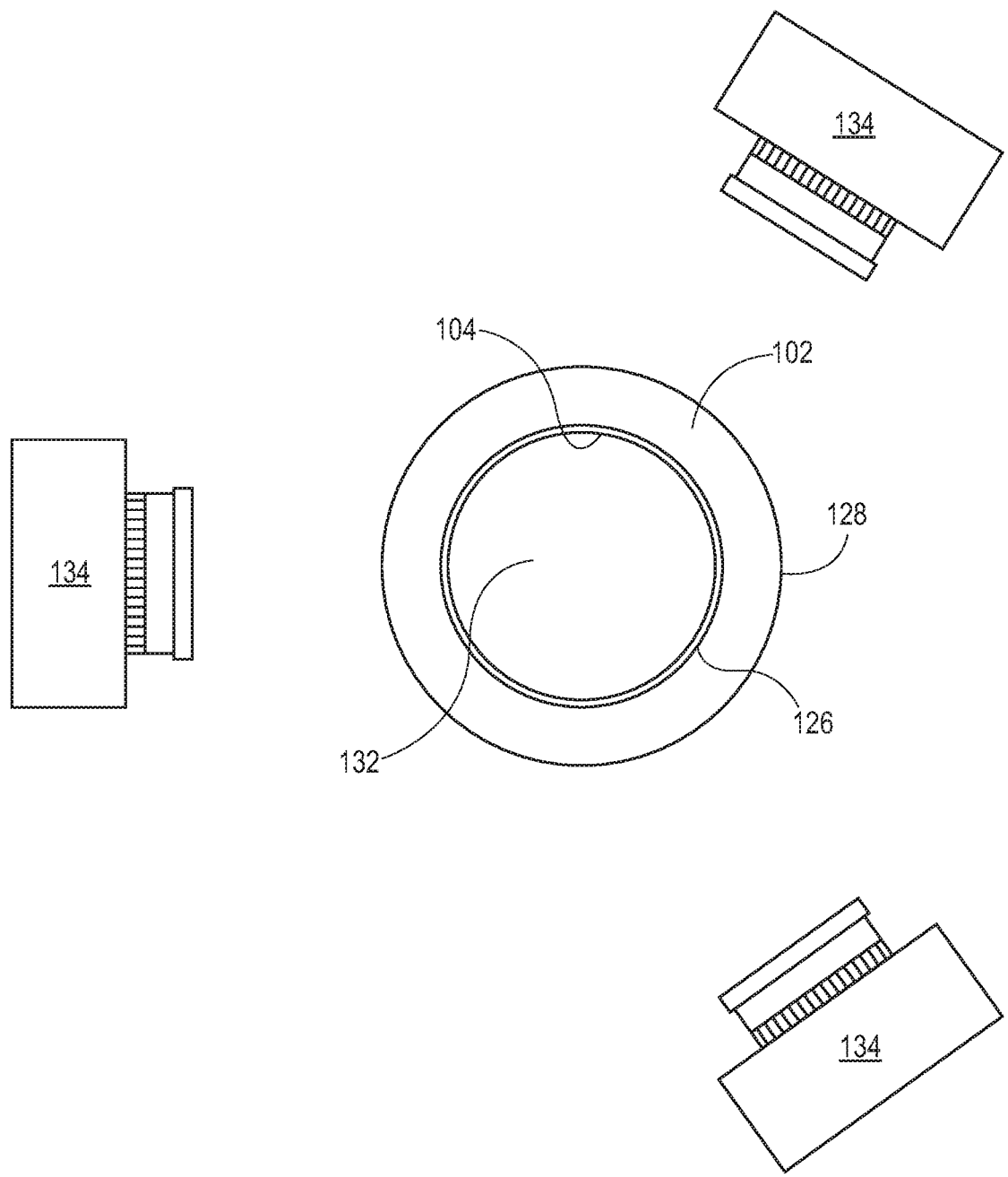
FIG. 1D is a top cross-sectional view of an implantable medical device installed in a testing system equipped to use the inventive methods described herein.

Referring now to FIG. 1D, cameras 134 are shown in relation to a mock vessel 102 in a testing system 100. In various embodiments, only one or two cameras may be necessary, or one camera and two mirrors may be utilized to capture an image of the test article 104 from various directions. In some embodiments, only one camera is utilized and the test article is only captured from one side. In some embodiments, the cameras 134 may be translated or moved by components of the system so that the cameras 134 are positioned to sequentially capture images of more than one test article 104 in multiple mock vessels 102. In various embodiments, the cameras 134 are optically, electronically, or otherwise connected to the signal processor.

In some embodiments, the signal processor is able to trigger the notification device to alert a user to the automatic detection of a failure event. In various embodiments, the notification device may send an electronic message to a user or system, store a record in a database or file system, activate a light or other output signal, or otherwise provide a sign that a predetermined condition or event has occurred with respect to the test article. In other embodiments the processing may occur at a later time after testing is completed, and notification is of failure identification is given after the processing of all captured images.

In some embodiments, the signal processor receives images captured by the camera and optionally processes them to identify when a failure has occurred with the test article. In some embodiments, the signal processor processes the images to generate data values for characteristic parameters that characterize the condition of the test article in the captured image. These characteristic parameters include many different types of measures of the characteristics of the test article resulting from numerous different image processing techniques as described in more detail herein. In various embodiments, the signal processor is capable of processing each image to assign data values to the characteristic parameters of the test article. In various embodiments, the signal processor may cause the camera to capture an image at a desired time to form a set of images for processing, or may receive a stream or sequence of images taken by the camera independently from which a set of images is selected for processing, or it may receive a video stream generated by the camera. In some cases the set of images used for processing may be the same as the sequence of images received from the camera.

In some embodiments, the signal processor, or some portion of the functions of the signal processor, are performed by systems disposed on or incorporated into the camera 118. In some embodiments, some or all of the functions of the signal processor are performed by either a specifically designed processor or a general purpose computer running software for signal processing attached to the camera for receiving and storing an image signal from the camera.

The camera 134 is subject to the typical lighting, resolution, shutter speed, depth of field, and picture transfer rate constraints of normal photography. The lighting must be able to provide adequate contrast to see all elements of the stent or other device being tested, and any support devices. The resolution must be high enough to capture enough pixels at no lower than the lowest resolution required in order to assess any change in shape of the test article. In some embodiments, the shutter speed is a minimum of 2.5 times the rate of change in the picture. For example, if testing is performed with a simulated pulse rate of 60 Hz, a preferred embodiment of the system and method would utilize a shutter speed of at least 1/(60*2.5)=6 ms or faster to avoid motion blur. Faster shutter speeds may be preferable if lighting conditions are sufficient to avoid image darkening, low contrast ratios, or other image degradation.

The depth of field of the camera is also relevant to the inventive system. Depth of field describes the focal plane with respect to the object of interest. A narrow depth of field results in blurring of any content outside the focal plane, whether farther away from or closer to the camera. A wide depth of field as found in a classic pin-hole camera will maintain a sharp image for all objects whether or not they are in or close to the focal plane.

In some embodiments of the system, the camera may take many pictures with a narrow depth of field at different focal distances. The signal processor may then combine the images to create a single picture containing information in three dimensions with the ability to move backward or forward along the axis extending from the camera with respect to the object of interest with equal clarity. In some embodiments, the use of multiple pictures allows the system to monitor test articles in a third dimension that would not be possible in only two dimensions of a single image, including the failure of such structures.

In some embodiments that use the multi-picture processing, if the signal processor uses only the high frequency components of each image to build a composite picture, the result may be a very high contrast image. The high contrast of the image may improve the automatic determination of failure of the test article.

The picture transfer rate relates to how quickly an image is transferred from the imager (such as a CCD chip) to the signal processor. A high speed camera may be able to take very fast images but if the image is not transferred from the imager before the next image is taken the fast imager is of no use. The image must be transferred from the imager to some memory before the next picture is captured. Modern imagers have compression systems built directly onto the imager to reduce the resulting amount of data being sent to memory. An example of these kinds of compression include be the JPEG format for still images or any one of the MPEG standards for video data. When compression is used, the amount of data transferred to memory is inversely proportional to the compression ratio. The higher the compression, the fewer bits per picture will have to be transferred but information loss may offset the reduced size of the image data. The highest demand for memory bandwidth is from high resolution RAW images that are not compressed at all. For a high speed camera, the tradeoffs between picture resolution and frame rate are based on memory bandwidth, and a suitable balance of the two must be selected for each different application using the inventive system.

Some embodiments of the system may use another method to reduce the amount of image data that must be transferred from the camera to the signal processor. In this optional method, the imager only sends image data from a portion of the imager by cropping or "windowing" the captured image. In this method the imager crops the image data to reduce the number of pixels on both the x and y axis being used on the imager to reduce the data transferred from the camera for each image.

In various embodiments of the system, the signal processor may comprise a general purpose computer executing program code to process images received from the camera. In other embodiments, the signal processor may comprise specific computer components, such as a dedicated graphics processor, or specially designed digital computer systems (such as application specific integrated circuits) and object code or firmware designed to process images received from the camera. In some embodiments, the signal processor may have local data storage for use in some methods of data analysis described below, or it may have access via a data network to network resources capable of receiving, storing, and retrieving images and data related to image analysis. Such network resources may include database resources, file system resources, or other types of data access resources, as may be developed in the future. In some embodiments the signal processor may be integrated into the camera to provide high speed access to images as they are captured by the camera. In some embodiments, some portion of the functions of the signal processor may be performed by the camera, or by a remote processor without departing from the scope of the inventive system.

In various embodiments of the systems and methods described herein, the signal processor may utilize a variety of methods to analyze an image. The various embodiments of the method include steps to determine if there has been a change in the shape or structure of the test article at certain key moments. In some embodiments, the key moments include the times of specific simulated pressures in the test cycle. For example, in some applications, a failure in the form of a break in a test article may show up at the maximum pressure but not at lower pressures. Various embodiments of the system include a synchronization data associated with the image to allow the signal processor to select and analyze images take at the desired moment during the testing of the test article. The synchronization data may be metadata about the image that is stored in relation to the image in a database or file system, or it may be incorporated into the data comprising the captured image itself as described in relation to various embodiments of the system below.

In such cases an example of the method of automatic failure detection is to compare the most recent images of the test article at the moment of highest pressure in each pressure cycle. The images are evaluated to look for a change in the structure or shape of the test article due to fatiguing or breaking of some portion of the test article that occurred between the capture of recent images. Detection of changes in the images of a test article may be performed using a variety of methods in different embodiments of the system and methods. In some methods, the process may comprise the measurement of the location of specific points or objects in an image and noting a change in the location of the same point or object based on measurements from previously recorded image data. In other embodiments, the methods may comprise the calculation of statistical averages for images of the test article recorded at different times and determining differences in the spectral content of the images. Some embodiments of the methods comprise running auto-correlations or cross-correlations between images taken over time. Yet other embodiments of the methods of automatic failure detection comprise performing direct image to image comparisons to show any differences between images take at different times, or by calculating piece-wise linear approximations for the test article in multiple images, and comparing the approximations from images to determine if a shape change is occurring at some point in the test article. Some of these methods are discussed in more detail herein.

In various embodiments of the inventive method, a variety of methods to identify the time of a given image and to synchronize the image with a desired event or moment may be utilized by the system. Timestamps comprising a portion of the metadata stored in conjunction with image data file may be used as a timing reference or synchronization data by the signal processor. Due to the cyclical nature of much of the testing, the determinant of an image taken at a critical time such as maximum pressure provides an ability to predict the other images recorded at maximum pressure based upon the elapsed time between the two images. If the time differential between the timestamp on two images is a multiple of the cycle time of the test, then the two images were recorded at approximately the same point in the test cycle.

For example, given a 60 Hz testing frequency, the period for each cycle is $\frac{1}{60}$ s or 16.666 ms. The initial time of a certain point of interest in the cycle, such as the time of maximum pressure, is determined by processing a number of images a test article in detail to identify an image that meets the desired point in the cycle. If the test article is a stent or similar device, the point of maximum pressure is characterized as also being the time when the width of the top of the stent is at its maximum value. In such case, the top of the stent is selected since the edges of a stent normally deflect more than the middle of the stent when exposed to pressure differentials. This processing may take a while due to (i) the number of images that may have to be processed to find one that corresponds to the point of interest, and (ii) the amount of calculations required to process each image to find the maximum stent deflection.

In some embodiments, when an image is found that records the maximum width, the timestamp of that image provides a baseline time, tmax, from which the timestamp of other images of the cyclical point of interest may be identified for analysis. The next set of images that record a time of maximum pressure may be estimated by adding the cycle time of the test simulation to tmax. For example, if the period of the test cycle is 16.666 ms then the maximum pressure will reoccur at tmax pulse every multiple of 16.666 ms. Since there may be variation in the actual period time of the cycle, and the calculation of tmax is subject to some errors in the system, in some embodiments, a periodic verification of a new tmax, and the maximum pressure may be needed clear any errors in the frequency or timestamps calculations.

In some embodiments it may be undesirable to utilize the timestamp information from the image file. Sometime picture timestamps represent the time the image data entered into memory rather than the actual time that the picture was taken. This can work well on high end camera systems since the entire picture is captured in the same moment and then transferred to memory as an entire picture, however if lower cost cameras are utilized the parts of the image may actually be captured at different times.

Machine to Camera Indicator

In some embodiments of the inventive system and methods, indicator signals from the testing machine to the camera serve as synchronization data. This simplifies portions of the signal processing functions. In one such method, the time of the maximum and minimum pressure is signaled to the camera by the testing machine by one or more lights, such as an LED device 136 disposed in the field of view of the camera. In some embodiments, the signals are sent to the camera by activating a light of a certain color to show when the pressure is at its maximum point. For example, the testing machine may cause a green LED to turn on briefly when the pressure is at its maximum point. Similarly, the testing machine may cause the same or another LED to turn on with a red light when the pressure is at its minimum point. The signal processor then may automatically select only the images in which either the red or green lights are on, and discard the images where neither LED is on. If a multicolor LED is being used, the red and green lights will occur at the same location which may save processing time. In either case, the signal processing time for checking the color of a known location in the image is much less than analyzing each image for artifacts of maximum pressure such as test article deflection.

If the LED colors are unique in the images, meaning no other areas of red or green are present in the image, then a simple histogram for each image will show when bright red or green content is contained in the image. This method also requires less signal processing time or power then analyzing each image for artifacts of maximum pressure.

In some cases there may be a phase delay between the indicator signal light and the actual time of maximum or minimum pressure. In such cases, the time stamps of each image may be utilized to calculate a time differential if a phase delay is found between the indicator light and the actual pressure minimum and maximum at the test article. The time differential representing the phase delay can be added to the time stamp of the image with the indicator light turned on to identify the desired time. The image with a timestamp closest to the desired time may then be selected for further processing to determine if there has been a failure of the test article.

Figure 2A:
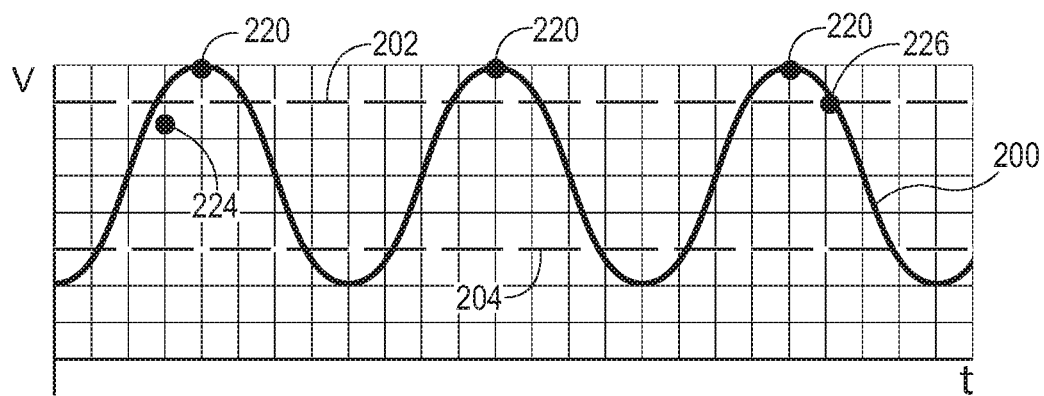
FIG. 2A is a depiction of a control signal for the pulsatile pressure pump of an embodiment of the inventive system.

Referring now to FIG. 2A, the control signals for the fluid pump and indicator lights 136 are depicted. Signal 200 depicts an example of a control signal driving the pulsatile pressure in the testing system 100 that is applied to a test article. In this example the control signal 200 is a sine wave, but in other applications, the control signal 200 may have other waveforms, and the waveform may vary over time. The control signal 200 may represent a voltage applied to a pump to pulse the flow of fluid through the test article, or it may represent some other signal used to control the mechanics of the testing system 100. The pressure cycle depicted by the signal 200 mimics the human pulse.

The testing system 100 generates pressure in the test article in response to control signal 200. In some embodiments, a pressure detector is used to measure a pressure signal or it may be deemed to be proportional to control signal 200. In other applications a parameter other than pressure may be selected for measurement. Various pressure thresholds 202 and 204 may be defined by a user of the system as values of interest to trigger the indicator lights. In the depicted embodiment of the control system, a high pressure threshold 202 is set to trigger when the control signal 200 exceeds the value 202. Similarly a low pressure threshold 204 is defined to trigger when the control signal 200 drops below value 204.

Figure 2B:
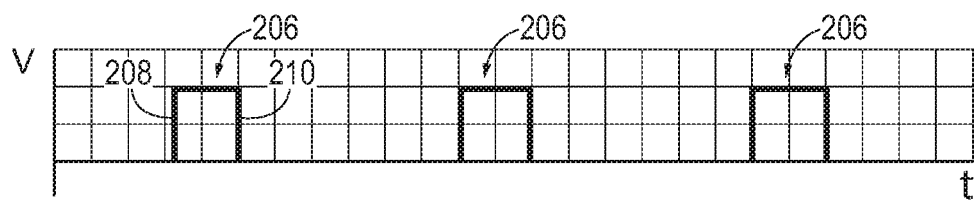
FIG. 2B is a depiction of a control signal for indicator lights in an embodiment of the inventive system.

Referring now to FIG. 2B, an embodiment of a control signal for light 134 is depicted. In some embodiments, when the control signal 200, and thus pressure in the mock vessel, reaches a positive peak value or exceeds threshold 202, the voltage applied to the green light 134 is raised to turn the light on at time 208. Once the signal 200 drops below the user defined threshold 202, the voltage to the green light is reduced at time 210 to turn the light off, thus each pulse 206 represents a pulse of voltage having a non-zero width. This pulse generates a flash of light from the green light each time the control signal 200 exceeds the threshold 202 or reaches a positive peak. In some embodiments, the pulse may be initiated when the control signal 200 exceeds the user defined threshold 202 instead of at the actual peak of the control signal 200.

Figure 2C:
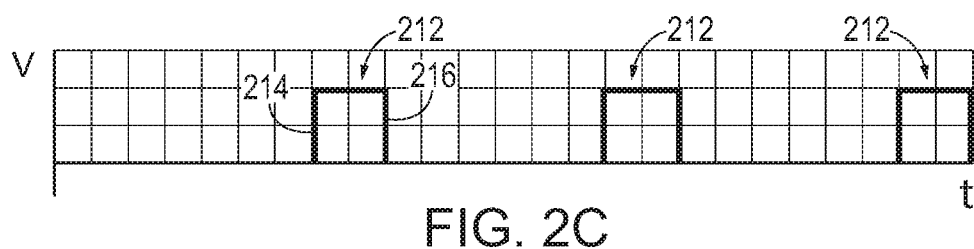
FIG. 2C is a depiction of a control signal for indicator lights in an embodiment of the inventive system.

Referring now to FIG. 2C, an embodiment of a control signal for light 134 is depicted. Similarly, when the control signal 200, and thus when pressure in the mock vessel, falls below low pressure threshold 204, or reaches a negative peak, the voltage applied to a red light 134 may be raised to turn the light 134 on at time 214. Once the signal 200 rises above the user defined threshold 204, the voltage to the red light 134 is reduced to turn the light off, thus each pulse 212 represents a pulse of voltage having a non-zero width. This pulse 212 generates a flash of light from the red light 134 each time the control signal 200 reaches a negative peak or drops below the threshold 204. In some embodiments as depicted in the figures, the pulse may be initiated when the control signal drops below the user defined threshold 206 instead of at the actual minimum value of the control signal 200.

Figure 2D:
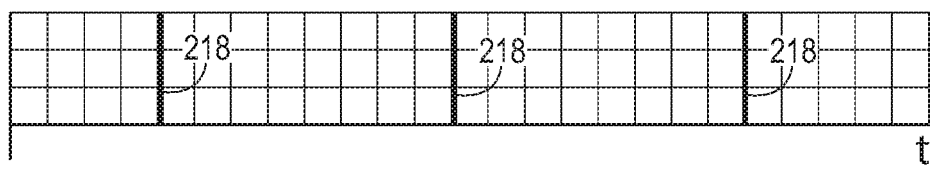
FIG. 2D is a depiction of a shutter control signal for a camera in an embodiment of the inventive system.
Figure 2E:
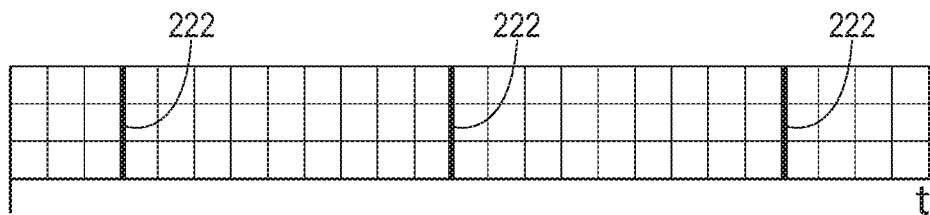
FIG. 2E is a depiction of a shutter control signal for a camera in an embodiment of the inventive system.

Referring now to FIGS. 2D and 2E, control signals for camera 134 are depicted in relation to the pressure cycle and control signal 200. At various times during the pressure cycle of the testing system 100, the camera 134 will capture an image and send it to the signal processor for storage or processing simultaneously or at a later time. Trigger signals 218 and 222 represent signals from the signal processor or other control system for camera 134 for the capture of an image. Points 220, 224, and 226 represent the corresponding points on the control signal 200 at the time of image capture in this embodiment. These control signals are not necessarily representative of voltages or other simple signals, but may signify the occurrence of an event generated by firmware or software based on timing parameters, among other embodiments. In some embodiments, the camera 134 may capture images as fast as possible in a stream or sequence of image, and then the desired images for the desired points are selected from that sequence in a simultaneous filtering step or a post-processing step.

Referring to FIG. 2D, the control signal is designed to capture an image as close as possible to the point of maximum pressure 220 in each iteration of the cycle using methods such as those previously described above. The signal is shown capturing an image in each cycle but in some embodiments it may not capture an image every cycle but only after some number of intervening cycles. The capture of images at or near the peak of the pressure cycle is preferred for some methods of automatic comparison described below. This mode of capture is considered synchronous because it captures an image at approximately the same time in the pressure cycle in each iteration of the cycle, and is thus synchronized with the pressure cycle in the mock vessel 102. A stream or set of images captured at synchronous times in the pressure cycle may be referred to as synchronous images.

Referring to FIG. 2E, the control signal of pulses 222 is designed to capture a series of images taken at varying points in the pressure cycle. In the depicted embodiment, the image captured at 224 is before the pressure peak in that cycle, while the next image captured at time 220 is at or near the pressure peak, and the third image captured at time 226 is slightly after the pressure peak in that cycle. In additional pressure cycles not shown in the figure, the timing of the images captured by this embodiment may cycle through the entire pressure range, so that some images are captured at the lower pressures as well. This mode of capture is considered asynchronous because it is not synchronized with the pressure cycle in the mock vessel 102. A stream of images captured in asynchronous mode may be referred to as asynchronous images.

In some embodiments the camera 134 may capture all images sequentially necessary to for synchronous and asynchronous modes. The resulting stream or set of images may be used to generate a synchronous or asynchronous set of images for further processing as desired by the user or the system.

Figure 3:
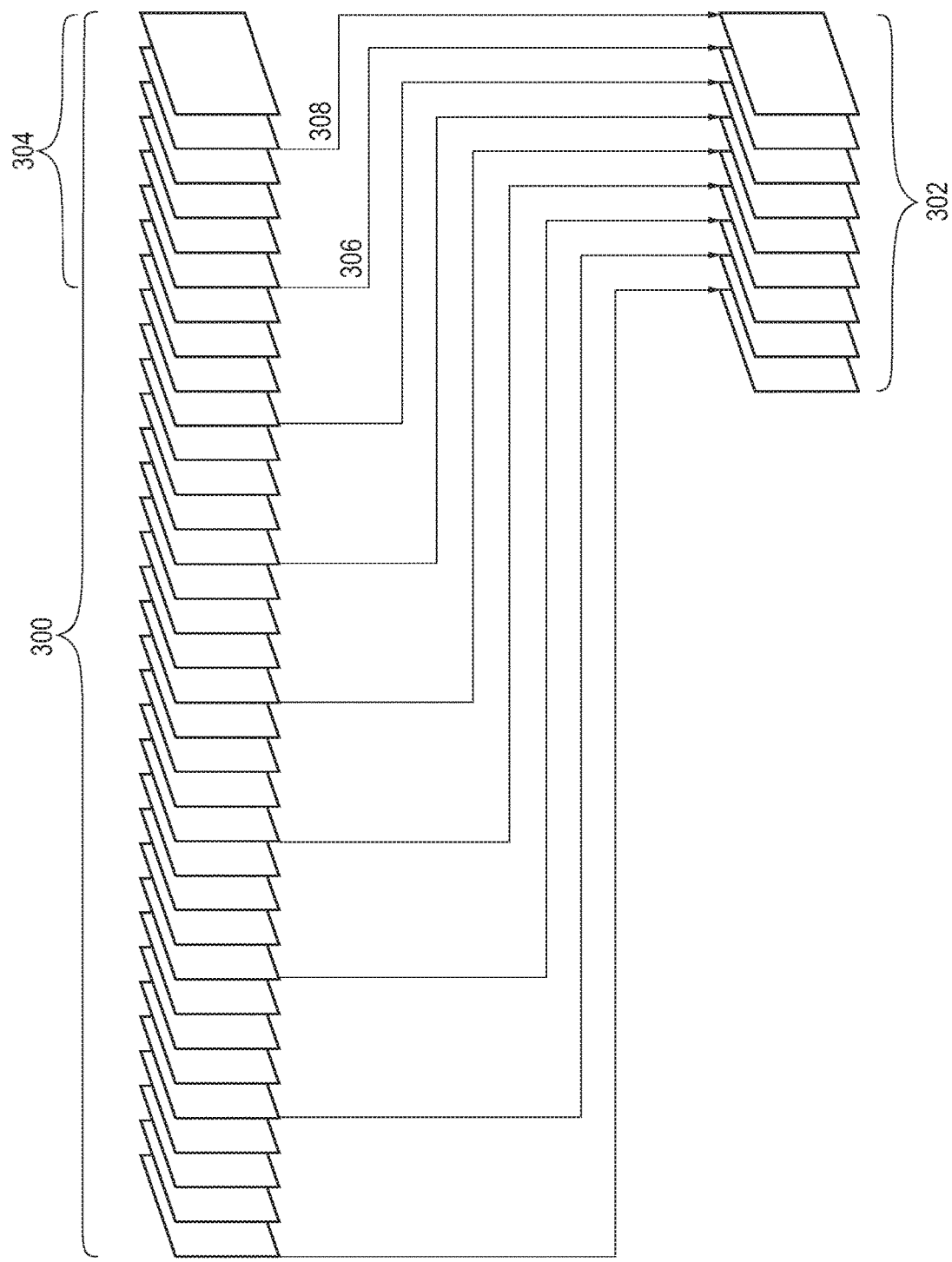
FIG. 3 is a schematic depiction of sets of images generated by an embodiment of the inventive system.

Referring now to FIG. 3, a logical representation of a set of images captured by a camera 134 using an embodiment of the system and methods described herein is depicted. The sequence 300 of images captured by camera 134 may comprise either a set of synchronous images, a set of asynchronous images, a combination of the foregoing, or a set of images taken at another interval such as at the maximum rate possible for camera 134. In some embodiments, set 134 may comprise a stream of images compressed using a video compression technology such as MPEG4.

In some embodiments of the inventive method of using the system, a subset 302 of images may be selected from the sequence 300 at certain intervals or at certain desired times. For example subset 302 may include every tenth image from sequence 300, although other intervals could be used, such as a capture time approximately 15 seconds after the prior selected image. Subset 302 results in a set with fewer images then 300 so the set may be processed in a shorter time to determine an approximate time of the occurrence of a failure event. In the depicted embodiment, the system and methods described herein identified a failure event between image 306 and image 308. To determine a more exact time for the failure event, a second subset 304 of the set 300 of images may be created using the images captured between image 306 and image 308. The subset 304 may then be processed to identify the time of failure more precisely. In various embodiments of the inventive system and methods, a number of different processing techniques may be utilized to identify the time of the failure event.

In some embodiments of the system and method, sequence 300 contains images captured in asynchronous mode and synchronous mode simultaneously. The sequence 300 may be filtered to a subset that includes only one or the other type of images. In some embodiments of the inventive system, the images in set 302 may be selected from set 300 using an interval that differs from the length of the pressure cycle to form set of asynchronous images. In other embodiments of the inventive system, all of the images in set 300 form an asynchronous set so that subset 302 is also formed of asynchronous images. In these embodiments, the set 302 of images are processed to form a video of the testing of the test article. This may be done by actually creating a compressed video format file such as MPEG4, or by simply displaying the images sequentially to create the appearance of movement.

When the asynchronous images in set 302 are viewed by a user of the system and method, the testing will appear to occur in a time-compressed manner and the asynchronous images will appear to be a slow motion video of the actual pulsatile testing of the test article. By viewing the video created from set 302 the failure events are typically clearly observable to a user of the system and method. Similar processes may be used on subset 304 to determine a more precise time for the failure event. Subset 304 may include every image in the stream of images, or it may constitute a shorter interval between selected images then used to create subset 302. Multiple iterations of "zooming" in to subsets with a shorter actual time duration but more of the original images from sequence 300 may be performed to reach a desired precision in the determination of the time of device failure.

In embodiments of the system and method in which automatic image processing will be used to identify the occurrence of a failure event, the set 300 of images may be captured synchronously, or set 302 may be selected to form a synchronous set of images from a set 300 of asynchronous images. In various embodiments of the system and methods described herein, the automatic image processing may preferably be performed on a set of asynchronous images.

Figure 4A:
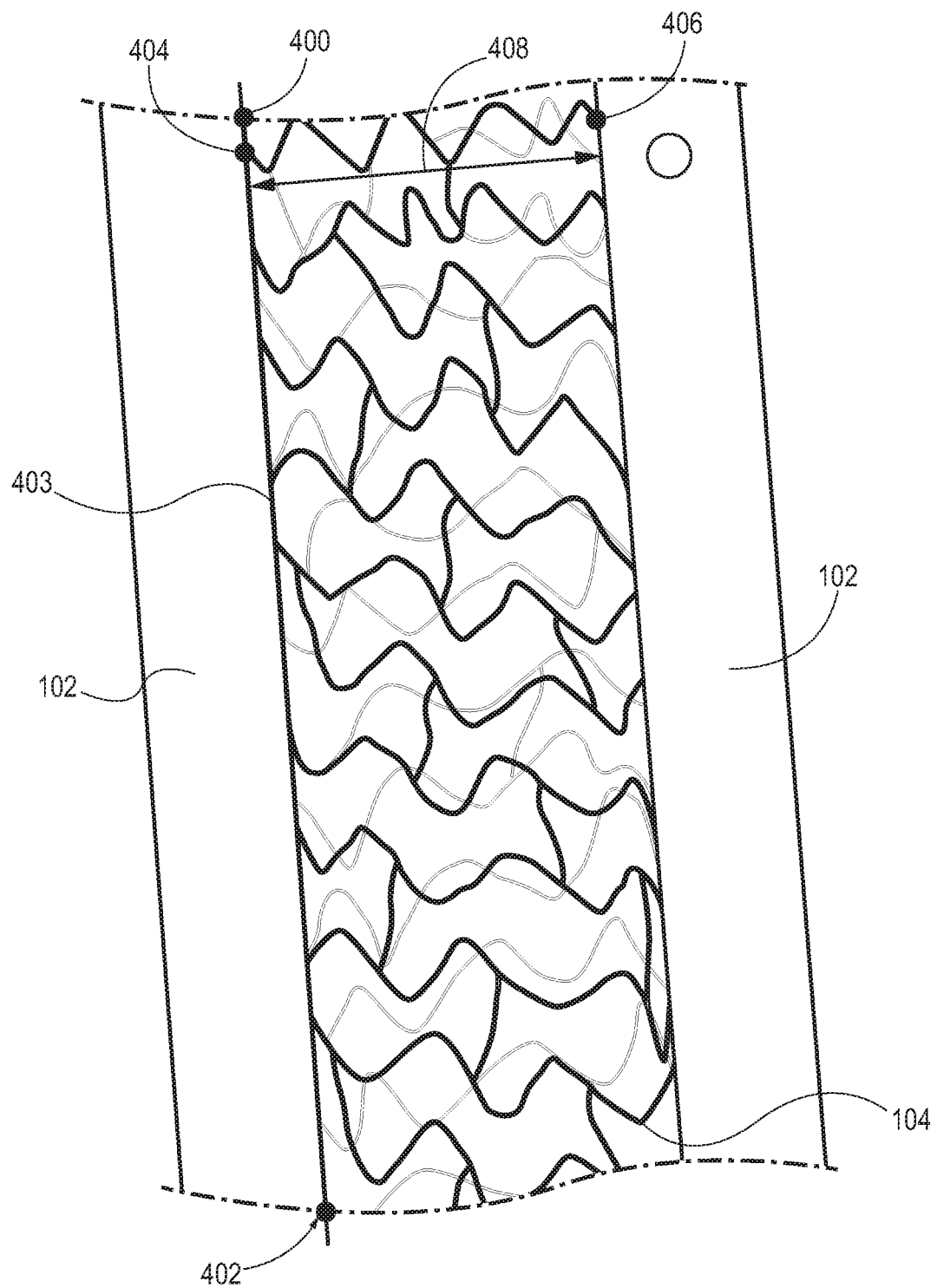
FIG. 4A is a detailed view of an implantable medical device installed in a testing system.
Figure 4B:
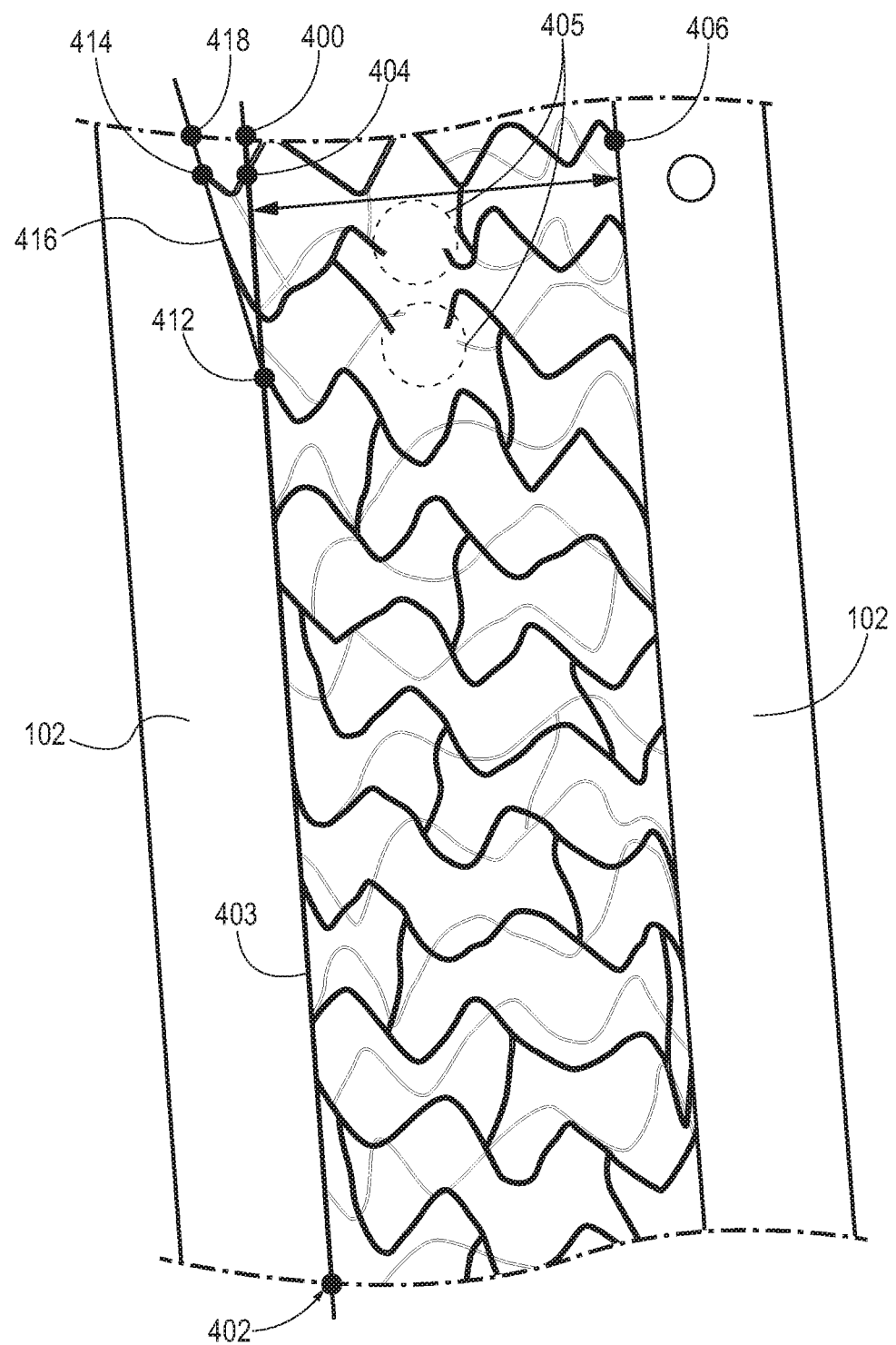
FIG. 4B is a detailed view of an implantable medical device installed in a testing system.

FIGS. 4A and 4B depict an example of images captured using an embodiment of the system and a method used therein for analyzing the images taken at maximum pressures, or at maximum and minimum pressures to automatically detect a failure of the test article. Line segment 400-402 in FIG. 4A represents a reference line tracing the outside of an unbroken test article, in this case of a stent. In some embodiments of the inventive system, the line segment 400-402 is automatically generated by processing the images to detect the left edge of the test article 403 on a reference image or images taken over time during testing prior to the failure event. This process may utilize any number of edge detection algorithms as would be known to one of skill in the art of image processing. In some embodiments, the line segment 400-402 may be repeatedly updated or recalculated using images captured at the minimum pressure or at the maximum pressure prior to occurrence of a failure event.

During testing, this line segment 400-402 may be used as a reference for comparison to the location of the edge of the test article 403 in images captured at high pressure such as that shown in FIG. 4B. This comparison may be performed by measuring the difference or "error" between the reference line 400-402 and one or more line segments detected on the test article 403 after the occurrence of a failure event. In the depicted example, a line segment 410-412 is shown in FIG. 4B. Line segment 410-412 as shown is a fit to a portion of the edge of the test article 403 as captured in an image taken at high pressure.

When the stent has not failed, the error is almost zero since the edge of the stent shown as line segment 400-402 is very close to the same location in both images. Once some wires in the test article 403 fail such at locations 405, the edge of the stent may expand, especially at the highest pressures, so that the edge captured in the images expands to line segment 410-412 near the broken wires 405. The difference between line segments 400-402 and 410-412 may be detected automatically by the signal processor using a variety of methods known to one of skill in the art. For example, in some embodiments the different slope of a line fit to the edges may differ above a threshold that indicates a break has occurred. In some embodiments, experimental determination of the threshold may be necessary to set parameters for automatic failure detection. The threshold will depend on the particular device being tested and the type of testing being performed (e.g. fatigue testing, fatigue to fracture testing).

Similarly, in some embodiments different lines fit to the varying segments 410-412 and 412-402 may also indicate that a break or failure event has occurred. In other embodiments, the measured distance from the point 404 on the detected edge 400-402 to point 406 on the opposite edge of the test article may increase to the distance from 406 to point 414 on line 410-412 after the failure event. The specific change in measured or calculated parameter or characteristic of the test article 403 or the line segments necessary to determine that a break or failure has occurred will vary depending on the characteristics of the mock vessel 102 and the test article 403. In some cases, experimental determination of thresholds for these parameters may be necessary prior to execution of automatic detection test runs.

In another embodiment of the inventive system the measured width of the image of the stent at various locations may be of use in monitoring the testing and identifying the occurrence of a failure event. The width as measured on the image corresponds to the diameter of the cylindrical test article. A reference test article width may be calculated along line segment 400-402 shown in FIG. 4A across any point along the length of the test article to the point on the opposite edge. For example, points 404 and 406 maybe used to calculate a reference width at that point. Widths may be determined at a few chosen points or across every pixel row for the length of the test article in the image. When the wires in the test article 403 fail at 405 the test article 403 will bulge in diameter near the failure point when the pressure in the mock vessel 102 is at its maximum value. In some cases the stent may return to its original diameter at the minimum pressure. Stent widths or diameters may be calculated from images captured at the maximum pressure such as the image shown in FIG. 4B. The system may automatically detect a failure by comparing the length of line segment 404-406 to the length of line segment 414-406. The difference in length, represented by line segment 414-404 is approximately zero while the test article 403 is in working order. Upon failure of the test article 403, the difference becomes significant. In some embodiments, a threshold value is provided for the length of 414-404 prior to determination that a failure has occurred. This threshold value may vary based on the size of the mock vessel, the pressure utilized in the system, and other parameters of the mock vessel and the test article.

If the difference in stent width is greater than the set threshold, a light or some form of alarm may provide notification that a change has occurred in the width of the test article. The automated system may keep taking the measurements and their changes over time along with all of the pressure, temperature, and frequency information to help construct expected life or failure plots for the test article.

In some embodiments, a history of images taken at high pressures and the measurements taken from those images may be maintained in a database. Such images may be statistically processed to measure the failure over time.

In some embodiments, the inventive system may utilize a method of comparing recently captured low and high pressure images to measure changes in the test article as a function of pressure. In typical cases, the high pressure images will show the stent break points or other failures while the low pressure images will not show any evidence of a break or other failure in the stent.

In some embodiments, if only a mock vessel and no test article is in the image, the thickness of the walls of the mock vessel and the inside diameter of the mock vessel may be measured as a function of pressure to help estimate compliance of the mock vessel. This may be useful with respect to optimizing the test pressures and characterizing the tests appropriately.

In images of the test article it may be desired to employ additional image processing steps to characterize the condition of the test article. In one embodiment of the system for use with wire mesh stents, the image may be processed to locate the wires that form the wire mesh of the test article. In an example process, an initial pixel that represents a part of the wire mesh is selected from an edge of the image. This pixel may be selected based on the color value of the pixel after contrast optimization. This method may be used to identify other structural components of a test article in addition to wire mesh structures.

Pixels adjacent to the initial pixel are then tested to determine if they also are part of the image that represent the wire mesh. Any adjacent pixels that are determined to be part of the wire mesh, based on color value, for example, are marked as such and a recursive search is performed connecting the like adjacent pixels to form a set of pixels that form a common color which represents a common structure. This processing results in a chain of data points that represents all or a substantial portion of the image corresponding to the stent structure.

Another method of detecting a change in the structure of the test article with increased sensitivity to change is to calculate the mean value from a sum of all moments from each pixel in the set with respect to the known pixel. A change in this value also indicates a break in the wire mesh of a stent.

In another optional method, one image is subtracted from another on a pixel wise basis. In one example of this method, the difference between an image take at or near the time of lowest pressure in the mock vessel and an image taken at or near the time of highest pressure is prepared, and peaks in the differential image represent structural changes caused by the varying pressure in the mock vessel. Such changes in the structure are indicative of a failure in the structure of the test article. In another example of this method, both images may be taken at or near times of highest pressure in the mock vessel, but one may be a reference image when the test article is known to be working properly. In some methods, the actual parameter of change is the size of the total image, and no pixel wise differentiation is performed.

Another method of signal processing used in some embodiments of the system and methods apply image processing algorithms to the images prior to utilizing specific failure detection algorithms to determine the occurrence of a failure event. The signal processor may utilize a variety of image processing algorithms to optimize the contrast of the image and visibility of the wire mesh structure of the test article. In some embodiments, this optimization step comprises converting the image from a color representation to a black and white representation or using color filters to help eliminate background colors from the image.

In some embodiments, the signal processor may perform additional image processing steps to further improve the contrast of the image and further highlight the structure of the test article. For example, the signal processor may apply an edge filter to the image. Exemplary edge filters include a two dimensional Sobel filter or a histogram equalization filter, though other filters may be utilized in various embodiments as will be clear to one of knowledge in the art of image processing. Selection of an appropriate filter may depend on the application and type of medical device to be tested. In the example of a stent-type medical device the Sobel filter results in better isolation of the test article, while the histogram equalization filter does not remove some unwanted elements from the image. For example, the walls of the mock vessel are highly visible in the histogram equalization while they disappear in the Sobel filtering.

After optimizing the contrast and applying other desired image processing to the image, measurements can be performed as described with reference to the automatic failure detection.

Statistical Line Processing

Figure 5A:
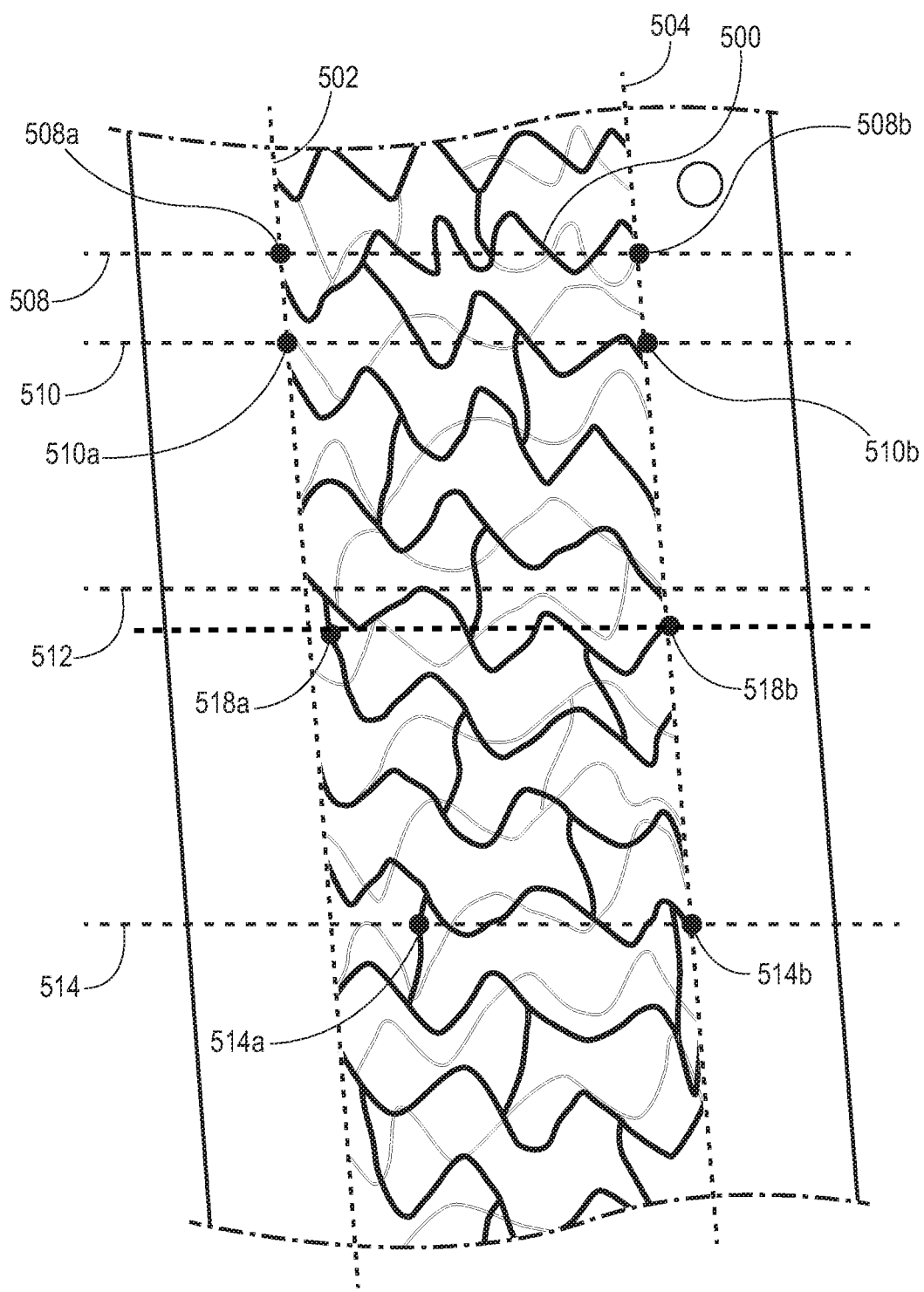
FIG. 5A is a detailed view of an implantable medical device installed in a testing system.
Figure 5B:
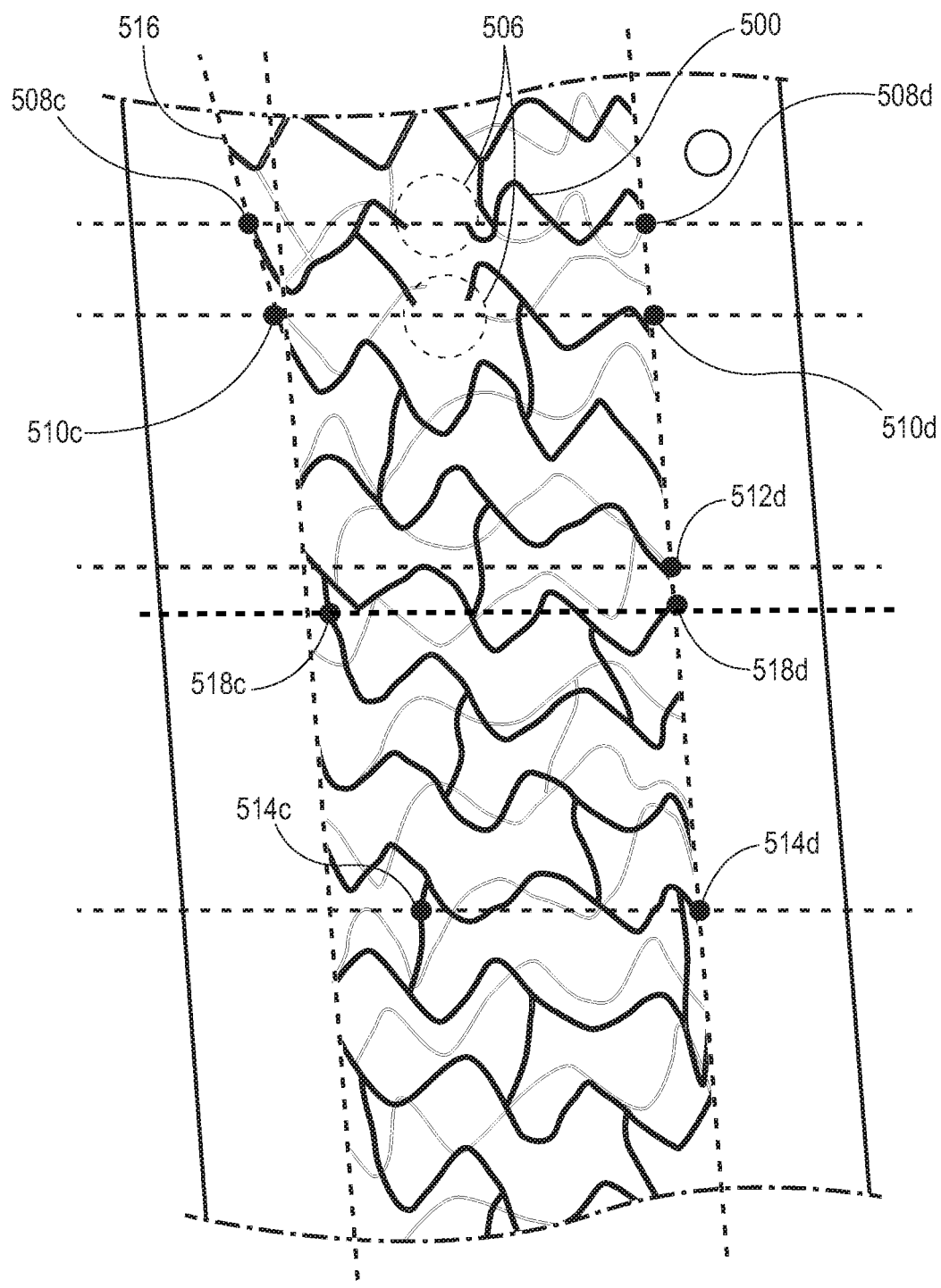
FIG. 5B is a detailed view of an implantable medical device installed in a testing system.

A method described in relation to FIGS. 5A and 5B may be used in some embodiments of the inventive system to quickly and automatically process images of irregularly shaped objects to detect changes in their shape. In summary, the method involves performing certain measurements on each row or column of pixels in the image, filtering the results of the processing to only the areas of first order interest that are easy to process and meet certain criteria, and then using statistics to determine when there is a change in the control parameters that represents a change in the structure of the test article.

After an image has been captured, filters such as those previously described above may be applied to enhance the edges of objects showing in the image using histogram equalization or another similar filter. Since in some cases the image may also show the mock vessel, in some embodiments the ends of the rows of pixels may be truncated at the software search boundaries 502 and 504 on each side to exclude the mock vessel boundary from the analysis. In some cases the image is not actually cropped or truncated but the signal processor ignores the portion of the images outside the software search boundaries.

In various embodiments of this method the signal processor measures the distance for each row of pixels in the image from the first dark pixel (identified by points 508a, 510a, 512a, 514a, 518a) starting from the left side of the image to the last dark pixel (identified by points 508b, 510b, 512b, 514b, 518b) closest to the right side of the image within the software search boundaries 501 and 503. In some rows, this measurement equals the actual width of the test article as in line 512 in FIG. 5A. The width of the test article is a known parameter for each test article.

However, the test article may have an irregular shape due to the requirements of the balloon deployment method and the use of wire mesh to form the test article. Referring to FIG. 5A, the measured boundaries on lines 508 and 510 represent lines that show roughly the actual width of the test article, while the measured boundaries on lines 514 and 518 go far into the interior of the stent before finding the first dark pixel because of a gap between wires in the wire mesh which results in a width much less than the real width of the test article. In order to prevent these shorter boundaries from distorting the results, in some embodiments the following filtering is applied to the measured boundaries distances. The measured boundary points and the distance between them are filtered to remove any measured widths for the test article that are not within some percent (such as +/−10%) of the actual known width of the test article. This filter may result in 50 to 70 percent of the rows being retained as accurate measurements, while the rest of the distance measurements for other rows are discarded or ignored by following steps in the process.

The filtered, measured data on row number, left and right boundary points, and boundary difference value may be stored for each image in a database. This will be accurate even if the stent is mounted at an angle so long as the angle is not so large that it increases the horizontal width of the test article more than the tolerance threshold (set at 10% in the above example).

Next the statistical averages of each measured parameter are calculated, including the number of lines that meet the requirements, the average left starting point, the average right starting point, and the average difference between starting points. The left edge of the stent can now be represented by one line 502 established by the average of the left starting points. The right edge can also be represented by one line 504 based on the average right starting points. This data may also be stored in the database.

The slope of the left edge line may be determined from points 510a and 512a using the basic formula of equal slopes: $(y-y1)/(x-x1)=(y2-y1)/(x2-x1)$ and solve for y in terms of x. The signal processor may also perform the same calculation using the right edges 510b and 512b. The system may also save this data in a database for as many line segments as are needed or desired. Over time, these slope intercept equations will be approximately the same until a fracture or other failure occurs in the test article.

When there is a failure of the structure of the test article, a portion of the boundary of the test article will diverge from its pre-failure boundary as determined according to the process set forth above. This divergent boundary segment is shown as the line 516 in FIG. 5B. This divergent line segment shows a deviation from the original line and implies a possible fracture or other failure in the test article.

Referring to FIG. 5B, lines 508 and 510 pass through the bulge allowed by the broken wires 506. Those two lines are processed in the image of FIG. 5B, points 508c and 510c will result in a calculation of the the slope intercept equation to represent the vertical left edge of the stent test article in the bulging area. An analysis of the equations from the database will show a point where the equations started to vary from those of historical calculations. If the variation or change is greater than a set threshold, an alarm is issued or notification sent to a user. The change could occur on either the left or right edge, at the top or bottom of the test article, or at any point where the system is defining the automatic slope intercept equations. The use of the database gives a very compact method of storing the analysis results over the history of the test for a specific test article. The database may be as simple as a data file or may utilize relational or other types of database storage software.

In some embodiments of the system, the notification of a potential failure event may trigger further changes in the operation of the inventive system. For example, the inventive system may monitor images of the entire test article until a fracture is detected. At the notification of the fracture or other failure, the camera may zoom in or center the image at the fracture location to capture enhanced images of the fracture as it continues to fail over time. If the test continues, the images will capture more details of how the test article deteriorates once the fracture begins.

If uncertainty is found in the processing, the lighting, camera focus, or camera angle may be modified to optimize the characteristics of the captured image. The signal processor may also determine an area of interest based on the areas that are changing in the image and modify the captured rectangle on the image to reduce the number of pixels in the captured image. As mentioned previously, reducing the number of pixels in the picture will allow faster image captures and reduce the processing time of each image. For example, a 2592 row×1944 column pixel imager has 2592×1944=5,038,848 pixels. If signal processing shows that only rows from rows 500 to 2000, and columns from 60 to 1700, comprising only 1500×1640=2,460,000 pixels, are necessary to capture the failure of the test article then only those portions of the camera's imager will be captured and processed by the system. This reduces the image size by one half to speed up image capture and processing time.

Search Area Methods

Figure 6:
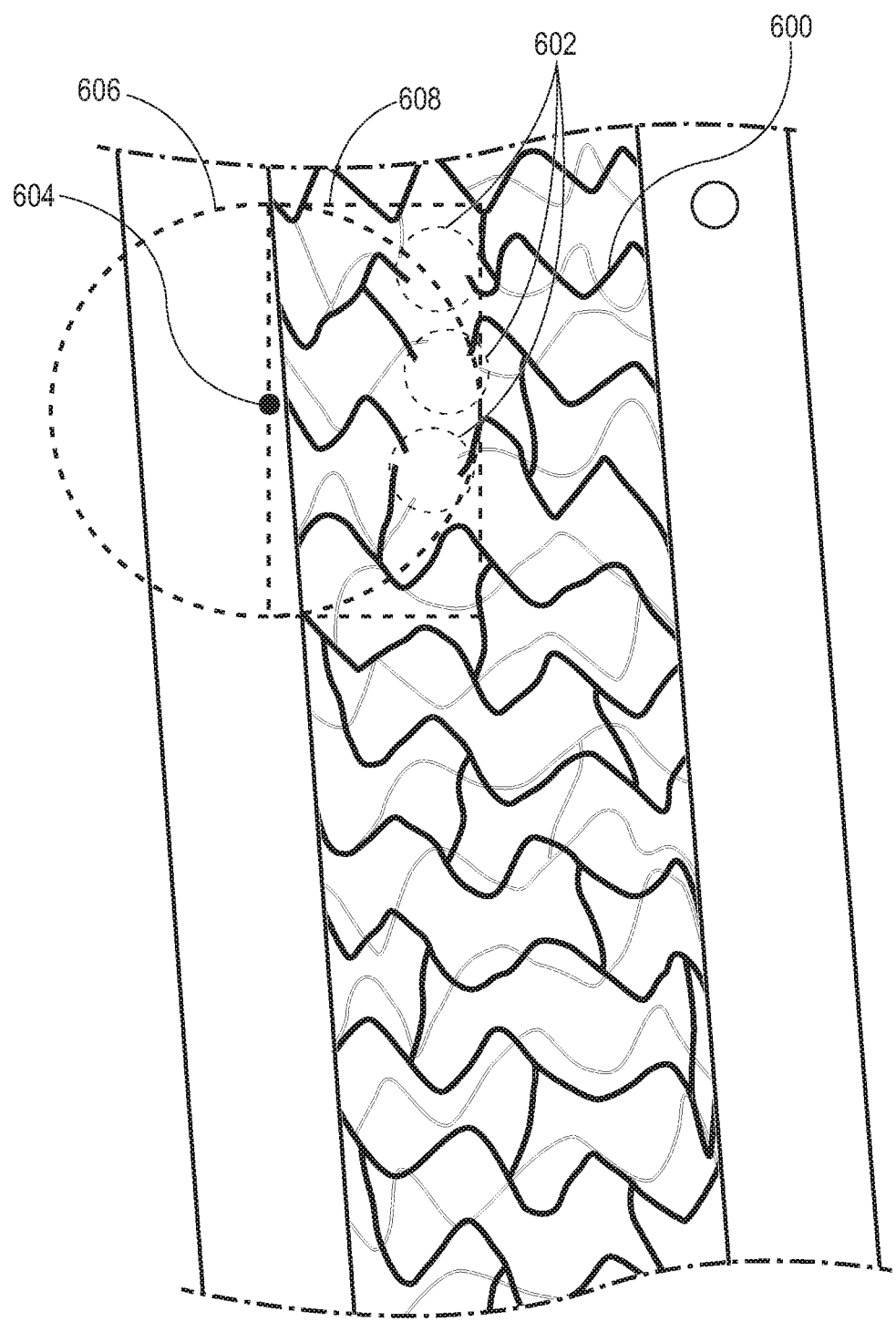
FIG. 6 is a detailed view of an implantable medical device installed in a testing system.

In some embodiments, the selection of adjacent pixels may be all pixels within a search area defined in relation to a pixel previously known to be representative of part of the wire mesh. Referring now to FIG. 6, an example image of a test article 600 with broken wires 602 in a mock vessel is depicted with example search areas shown thereon. The search area may be a circle 606 with the radius of R from the known pixel 604, a rectangle 608 with the known pixel 604 in the center or on some defined edge, or any geometric shape such as a semi-circle or polygon, or any combination thereof.

The signal processor may continue identifying pixels representative of the wires in the wire mesh by finding all adjacent pixels within the search area. The number of pixels found in the search is representative of the amount of connected stent material within the boundary of the search area. The analysis of the same search area over time may be used as a basis for comparison of changes in the test article. For example the signal processor may compare the number of pixels of wire mesh are found in the search area in prior images with the number of pixels of wire mesh found in the most recent image. If the total number of pixels representing wire mesh is reduced in the most recent image it is indicative that a break has occurred at some point in the wire mesh in the search area. If the reduction in the number of identified pixels representing wire mesh is greater than an alarm threshold sent by a user of the system, than an alarm may be triggered or some other form of notification sent to the user or recorded in a database.

An alternative method of counting pixels representative of the structure of the test article is to define the total set of pixels in a selected search area such as those described above in relation to FIG. 6, and then count all pixels in the search area that are the same grey scale or color value as the known representative pixel or within a certain percent of that color value. Comparing past and present pixel counts within a search area may indicate a change in the structure of the test article.

Additional Methods for Improving Image Capture

Other methods of adjusting the image capture include: reducing the resolution in a close-up area of interest to allow a large increase in frame rates for video with less motion blur. If the frame rate timing of the camera is adjusted to synchronize with the frequency of the pressure waveform at the fundamental sampling rate of the video compression, then the phasing of the video may be timed so that the maximum pressure is at the beginning of a group of pictures for maximum resolution and accessibility. This is because many compressed video formats do not capture an entire image for each frame of a video stream, but instead capture certain key frames and only motion vectors and partial frames for intermediate frames in the video. Automatic techniques can be used to check for pixel values at a specific time in the video without reducing the entire video stream to individual pictures, which saves processing time. Analysis of the motion vectors in specific regions of the video frame may also indicate a change in the condition of the test article without having to view or decode all of the compressed video. This is known in the art of the video processing community. The processing will be different but the principle concepts will still apply for video and still picture photography.

Video Stream Processing

Video streams can also be analyzed to detect fractures or other failures in the stent or other test article. An example utilizes the MPEG video compression format. The MPEG video stream is usually made up of groups of pictures (GOP) in the form of IBBPBBPBBPBB where I represents an intra-coded picture, and B and P represent motion-compensated difference information. The I-picture or Intra-coded picture in a GOP does not contain any predictions from other pictures. These I-pictures are easily parsed from an MPEG stream, for example, by those skilled in the art and the remaining pictures in the stream can be discarded. These I-pictures can be extracted and saved as separate pictures or decoded and stored in another format. The time code in the streams can be used to synchronize the pictures with the min and max pressure signals or as discussed previously, analyzed to determine the greatest stent width in a picture to synchronize the remaining video from this reference. If all of the synchronized I-pictures are then re-encoded, the motion vectors within the encoded stream can be used to determine a change in the pictures. Decoding of all the pictures would not be required but only tracking the motion vectors within the re-encoded MPEG stream would serve as an indication of change within the picture group. This would greatly simplify the processing over the length of the test. An alternate method would be to simply track the file size of the pictures. When motion occurs, a larger file will result from the motion vectors being added.

This is very similar to JPEGs where the pictures are subtracted. The greater the differences, the larger the difference file size.

Alternate Camera Considerations

Expensive camera systems have the advantages of having many lenses available for specific uses, very fast shutters, larger imagers for more light sensitivity, a wide variety of resolutions, and very fast transfer rates to memory. There are disadvantages to such camera systems, including being too expensive for multi-camera setups, requiring sophisticated computer control be performed only through the manufacturers software, camera weight may be too high for platforms moved using stepper motors, required use of high end hardware and software for processing the image sizes or amount of content being delivered by the camera system.

Lower cost camera systems have advantages including much lower cost as compared to high end cameras allowing multiple cameras on a single testing machine without undue cost, light weight cameras are compatible with stepping motor controller platforms, simple to control due to limited commands, and provide a variety of video and image format options. The disadvantages of the low cost camera include a rolling shutter, limited low light performance, motion blur, long term availability of a given camera system may be limited, and internal signal processing may limit or have unknown effects on the output images. Some methods for overcoming the disadvantages of the low cost cameras allow them to be used in the inventive system without compromising the ability to automatically detect failures in the test article.

Alternative Imaging System and Method

In some alternative embodiments of the system a single camera is utilized to capture images of multiple test articles and multiple views of the same test article. As can be seen in FIG. 1, multiple test articles may be simultaneously tested in a single embodiment of the inventive system. It may be preferred to utilize a single camera to capture images of all the test articles in sequence.

In this embodiment, multiple test articles are simultaneously tested in the testing system. The test articles may be arranged in a line, or in a circular configuration as shown in FIG. 1, among other possible configurations. The camera 134 is moveably mounted onto a rail. The rail is provided with actuators (e.g., electric, pneumatic, stepper motors) to move the camera 134 along the rail in a controlled manner. Using this embodiment of the system, a large number of test articles may be monitored using a single camera 134 thus reducing cost and complexity of the system.

In some embodiments, mirrors may be mounted in relation to the test articles to allow a single camera 134 to capture images of the sides of the test articles facing away from the camera 134. This alternative is the system as shown in FIG. 1D with two of the cameras 134 replaced with mirrors that are both in the field of view of the single camera 134 and oriented to reflect the opposite side of the test article back to the single camera 134. This may greatly increase the accuracy of the system in detecting failure of the test article as soon as it occurs, since failures on the side of the test article away from the camera might not be detected from images captured of the other side of the test article.

In some embodiments, mirrors may be mounted on actuators to allow the mirrors 1308 to be pivoted in relationship to their mount. This pivotal movement allows various images to be captured by camera 134 as it passes by a test article. The images may be processed separately or combined to form a single image of the entire surface of the test article before processing to detect failures of the test article.

Additional Data Processing Structures

In some embodiments of the system, a large array of low cost cameras could be directed at multiple test articles, sending captured images to a common signal processor such as a powerful computer to process all of the images. Each test article may have a unique bar code or other identifier in the field of view of the camera that allows identification of the test article during post processing of the images. In some embodiments, the camera may be mounted on a track, translation table, or other similar device, where stepping motors can move the camera around the test article during testing. These images may then be stitched or otherwise processed together to make a more detailed image of the test article for further analysis.

In some embodiments, camera resolution, focus, and position may be modified based on feedback from the processing results to provide more detail or more information when there is uncertainty in the processing or the need for clarification of some parameter in the present setup.

In some embodiments, the signal processor may automatically crop the images to an area containing an area or object of interest, or to extract a feature of interest for use in correlation functions, or to reduce the size of the database of images collected during the test.

In some embodiments, the system may include a measurement reference such as a ruler or standard unit next to each test article in the field of view of the camera to allow automatic calibration of the image. The signal processor may also scale the images so that all images of a given test article have the same scale for comparative analysis.

Other embodiments of the system may utilize a camera having a narrow depth of field that is mounted on a platform for translation. If the camera is moved toward or away from the test article multiple high resolution images of the test article may be captured at different depths in the test article. This enhancement may help to track specific structures through the test article.

The above-described systems and methods maintain an isolation wall between the test article and the camera system, meaning that the testing system does not alter its operation in response to the image analysis in most of the inventive methods. As a result, this system could be added to almost any stent or other device test system. Real time evaluation of deflection and compliance along with logging all of this data over time could be achieved with this same system. If the isolation is less important, the deflection results from the camera and signal processor could be fed back into the test controller to make a closed loop system to control the deflection and pressure applied to the test article based upon the feedback.

The Alarm or Notification

In some embodiments, the output of the automatic fracture detection system is an alarm, response, or notification of some nature. This response could be as simple as turning on a light to show that a change has occurred in a specific test article in the testing machine. Other forms of notification such as email, text messaging, or log file or database entries will be obvious to those of skill in this field. It could also trigger a response to modify the operation of the test machine to cause intense data collection and signals processing for the fractured stent to collect additional information about a test article that is beginning to show signs of fracturing.

The condition for any alarm, response, or notification would be triggered on thresholds set by a user or developer of the system. In some embodiments the trigger is the amount of deflection of the edge of the test article between minimum and maximum pressure states, the increased width of the test article in any area, a discontinuity in the structure analysis that was not there previously, an increase in the image differences based on either shapes or file size, increase or decrease in a cross-correlation function or auto-correlation function, or for video processing, an increase in the motion vectors found in the MPEG stream. The alarm may alter the frequency of capturing and saving images of the test article to capture the actual decay or breakdown of the fracturing test article or start video recording of the stent if a fast decay is expected.

The operating conditions of the test such as pressures or temperatures may be altered once a fracture has been detected to help model a different scenario than the original conditions leading up to the fracture.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A system for automatically identifying a failure of an implantable medical device during testing thereof, the system comprising:
a mock vessel having a lumen for receiving the implantable medical device;
a pump in fluidic communication with the mock vessel for pumping a fluid through the mock vessel in a pulsatile flow with a pressure cycle;
a camera for capturing a sequence of images of the implantable medical device;
a signal processor attached to the camera for receiving, storing, and processing the sequence of images;
wherein the signal processor processes the sequence of images to select a set of images taken at a selected time in the pressure cycle of the pulsatile flow;
wherein the signal processor processes the set of images to identify the failure of the implantable medical device;
wherein each image in the set of images is captured after a selected interval of time has elapsed after the capture of a preceding image; wherein the selected interval of time is less than or greater than the length of the pressure cycle.

2. The system of claim 1 wherein the selected time is the moment of highest fluid pressure in the lumen of the mock vessel during the pressure cycle.

3. The system of claim 1 wherein the images in the set of images comprise asynchronous images.

4. The system of claim 1 wherein the signal processor selects a subset of the set of images by selecting images from the set of images that are separated by a selected number of intervening images.

5. The system of claim 4 wherein the signal processor generates a video from the subset of the set of images.

6. The system of claim 1 wherein the sequence of images comprises both asynchronous images and synchronous images.

7. The system of claim 1 wherein each image in the set of images is captured when the pressure in the lumen of the mock vessel is greater than a high pressure threshold value.

8. The system of claim 7 further comprising a pressure indicator light in the field of view of the camera, the pressure indicator light configured to illuminate when the pressure in the lumen of the mock vessel is greater than the high pressure threshold value.

9. The system of claim 1 wherein the signal processor processes each image in the set of images to detect a characteristic of at least one edge of the implantable medical device and compare the characteristic to a characteristic of the edge detected in a preceding image in the sequence of images.

10. The system of claim 9 wherein the characteristic of each edge of the implantable medical device is a slope of a line fit to the edge of the implantable medical device.

11. The system of claim 9 wherein the characteristic of each edge is the distance from a point on the edge to a point on another edge.

12. The system of claim 1 wherein the signal processor processes each image in the set of images to detect at least one width measurement of the implantable medical device and compare the at least one width measurement to a width measurement detected in a preceding image in the set of images.

13. The system of claim 12 wherein the at least one width measurement is measured by selecting a line of pixels from the image and identifying the outermost pixels in that line of pixels that are representative of a structure of the implantable medical device.

14. The system of claim 13 wherein the implantable medical device is a stent and the structure of the implantable medical device is a wire component of the stent.

15. The system of claim 1 wherein the signal processor processes each image to measure at least one characteristic of the implantable medical device; and the at least one characteristic for each line in the plurality of lines in each image comprises a location of a left outermost pixel that is representative of the implantable medical device or a location of a right outermost pixel that is representative of the implantable medical device.

16. The system of claim 15 wherein the signal processor calculates a slope intercept formula for the at least one characteristic for at least two lines of pixels in each image.

17. The system of claim 16 where the signal processor identifies a change in the slope intercept formula for a subsequent image in the sequence of images as the failure of the implantable medical device.

18. The system of claim 1 wherein the signal processor selects a search area in each image in the sequence of images and measures a characteristic of the implantable medical device in the search area.

19. The system of claim 18 wherein the characteristic of the implantable medical device is the number of pixels in the search area representative of a structure of the implantable medical device.

20. The system of claim 19 wherein the implantable medical device is a stent and the structure of the implantable medical device is a wire mesh component.

21. The system of claim 1 wherein the implantable medical device is a stent formed of a wire mesh, and the signal processor selects pixels in each image representative of the wire mesh.

22. The system of claim 21 wherein the signal processor locates discontinuities in the pixels representative of the wire mesh to identify a failure of the implantable medical device.

23. The system of claim 21 wherein the signal processor calculates differences between the pixels representative of the wire mesh in a plurality of images in the sequence of images to identify a failure of the implantable medical device.

24. A method of using the system of claim 1 to automatically identify the occurrence of a failure event during testing of an implantable medical device, the method comprising the steps of: deploying the implantable medical device in the lumen of the mock vessel; attaching the lumen of the mock vessel to the pump; pumping a fluid through the mock vessel in a pulsatile flow having a pressure cycle; capturing a sequence of images of the implantable medical device; selecting a set of images from the sequence of images wherein each image is captured at a selected time in the pressure cycle; contemporaneously processing the images using the signal processor to identify the occurrence of the failure event wherein each image in the set of images is captured after a selected interval of time has elapsed after the capture of a preceding image; wherein the selected interval of time is less than or greater than the length of the pressure cycle.

25. The method of claim 24 wherein each image in the set of images is selected such that each image is separated from the preceding image in the set of images by a selected number of images in the sequence of images.

26. The method of claim 24 wherein each image in the set of images is captured when the pressure in the lumen of the mock vessel is greater than a high pressure threshold value.

27. The method of claim 24 wherein the system further comprises an indicator light in the field of view of the camera; and the method further comprises the steps of illuminating the indicator light when the pressure in the lumen of the mock vessel is greater than a high pressure threshold value; and the set of images is selected to include each image in the sequence of images wherein the indicator light is illuminated.

28. The method of claim 24 wherein the step of processing the images using the signal processor to identify the occurrence of the failure event further comprises the steps of:
   detecting a characteristic of at least one edge of the implantable medical device in each image in the set of images;
   comparing the characteristic to a characteristic of the edge detected in a preceding image in the set of images.

29. The method of claim 28 wherein the characteristic of at least one edge of the implantable medical device is a slope of a line fit to the at least one edge.

30. The method of claim 28 wherein the characteristic of at least one edge of the implantable medical device is the distance from a point on the edge to a point on a second edge.

31. The method of claim 24 wherein the step of processing the images using the signal processor to identify the occurrence of the failure event further comprises the steps of:
   detecting at least one width measurement of the implantable medical device in each image;
   comparing the at least one width measurement to a width measurement detected in a preceding image in the set of images.

32. The method of claim 31 wherein the step of detecting comprises the steps of:
   selecting a line of pixels from the image;
   identifying the outermost pixels in that line that are representative of a structure of the implantable medical device.

33. The method of claim 32 wherein the implantable medical device is a stent and the structure of the implantable medical device is a wire component of the stent.

34. The method of claim 24 wherein the step of processing the images using the signal processor to identify the occurrence of the failure event further comprises the steps of:
   detecting at least two pixels in each image representative of an edge of the implantable medical device;
   calculating a characteristic of the edge using the at least two pixels;
   comparing the characteristic of the edge in each image to the characteristic calculated from the preceding images in the set of images.

35. The method of claim 34 wherein the step of calculating a characteristic of the edge comprises calculating a slope intercept formula from the at least two pixels.

36. The method of claim 35 wherein the step of comparing the characteristic of the edge in each image comprises comparing the slope intercept formula of each image with the slope intercept of a preceding image.

37. The method of claim 35 wherein the step of comparing the characteristic of the edge in each image comprises comparing the slope intercept formula of each image to an average slope intercept of the preceding images in the set of images.

38. The method of claim 24 wherein the step of processing the images using the signal processor to identify the occurrence of the failure event further comprises the steps of:
   selecting a search area in each image in the set of images;
   measuring a characteristic of the implantable medical device in the search area.

39. The method of claim 38 wherein the characteristic of the implantable medical device in the search area is the number of pixels in the search area representative of a structure of the implantable medical device.

40. The method of claim 24 wherein the implantable medical device is a stent formed of a wire mesh, and the step of processing the images using the signal processor to identify the occurrence of the failure event comprises the steps of:
   identifying pixels representative of the wire mesh; and
   locating discontinuities in the pixels representative of the wire mesh.

41. An automatic failure detection system for detecting an event of failure of a test article subject to a pulsatile pressure cycle of a fluid in a mock vessel, the automatic detection system comprising:
   a camera for capturing a sequence of images of the test article;
   a signal processor connected to the camera to receive the sequence of images;
   the signal processor configured to contemporaneously process the sequence of images to automatically identify an event of failure of the test article;
   wherein the signal processor selects a first image and a second image from the sequence of images; and
   wherein the first image is an image of the test article during a first cycle of the pulsatile pressure cycle, and the second image is an image of the test article during a subsequent cycle of the pulsatile pressure cycle; and
   wherein the signal processor determines a value of at least one characteristic for the test article for the first image and the second image; and
   wherein the signal processor compares the values of the at least one characteristic for the test article for the first image and the second image to automatically identify structural changes in the test article representative of an event failure.

42. The automatic failure detection system of claim 41 wherein the at least one characteristic comprises the slope of a line fit to an edge of the test article.

43. The automatic failure detection system of claim 41 wherein the at least one characteristic comprises the width of the test article measured at at least one point.

44. The automatic failure detection system of claim 41 wherein the at least one characteristic comprises a number of pixels in a search area that are representative of the test article.

45. The automatic failure detection system of claim 41 wherein the at least one characteristic comprises a discontinuity in an image representing a break in the test article.

* * * * *